(12) United States Patent
Jovanov

(10) Patent No.: US 11,678,812 B1
(45) Date of Patent: Jun. 20, 2023

(54) SYSTEMS AND METHODS FOR MONITORING HYDRATION

(71) Applicant: Emil Jovanov, Huntsville, AL (US)

(72) Inventor: Emil Jovanov, Huntsville, AL (US)

(73) Assignee: Board of Trustees of the University of Alabama, for and on behalf of the University of Alabama in Huntsville, Huntsville, AL (US)

( * ) Notice: Subject to any disclaimer, the term of this patent is extended or adjusted under 35 U.S.C. 154(b) by 0 days.

(21) Appl. No.: 17/187,681

(22) Filed: Feb. 26, 2021

Related U.S. Application Data

(63) Continuation-in-part of application No. 16/174,163, filed on Oct. 29, 2018, which is a continuation-in-part of application No. 15/239,810, filed on Aug. 17, 2016, now Pat. No. 10,433,666.

(60) Provisional application No. 62/981,894, filed on Feb. 26, 2020, provisional application No. 62/578,209, filed on Oct. 27, 2017, provisional application No. 62/205,839, filed on Aug. 17, 2015, provisional application No. 62/241,494, filed on Oct. 14, 2015, (Continued)

(51) Int. Cl.
*A61B 5/05* (2021.01)
*A61B 5/0537* (2021.01)

(52) U.S. Cl.
CPC .................................. *A61B 5/0537* (2013.01)

(58) Field of Classification Search
CPC ... A61B 5/0537; A61B 5/6801; A61B 5/0024; A61B 5/02405
See application file for complete search history.

(56) References Cited

U.S. PATENT DOCUMENTS

| 3,391,547 A | 7/1968 | Kingston |
| 4,343,316 A | 8/1982 | Jespersen |
| 5,135,485 A | 8/1992 | Cohen et al. |

(Continued)

FOREIGN PATENT DOCUMENTS

| CN | 205054984 U | 3/2016 |
| EP | 3000385 A1 | 3/2016 |

(Continued)

OTHER PUBLICATIONS

Jovanov, et al., "Guest Editoral Body Sensor Networks: From Theory to Emerging Applications," IEEE Transactions on Information Technology in Biomedicine, Nov. 2009, pp. 859-863, vol. 13, No. 6.

(Continued)

*Primary Examiner* — Curtis B Odom
(74) *Attorney, Agent, or Firm* — Maynard Nexsen PC; Brian T. Sattizahn

(57) ABSTRACT

A smart object may be used to monitor the hydration level of a person. The object has at least two impedance sensors that can be used to sense the complex impedance of a person when a tissue of the user comes into contact with the impedance sensors. The measured impedance can then be used to determine the hydration level of the person. In addition to using the impedance sensors to determine the hydration level of the person, the impedance sensors can also be used to capture an electrocardiogram for the person. The smart object may also be used with another smart object to determine the identity of the user or other physiological parameters of the user such as blood pressure.

20 Claims, 29 Drawing Sheets

Related U.S. Application Data provisional application No. 62/330,692, filed on May 2, 2016.

(56) References Cited

U.S. PATENT DOCUMENTS

| | | | |
|---|---|---|---|
| 5,182,545 | A | 1/1993 | Goekler et al. |
| 7,928,835 | B1 | 4/2011 | Jovanov et al. |
| 8,574,165 | B2 | 11/2013 | Marsh |
| 8,754,769 | B2 | 6/2014 | Stein et al. |
| 8,863,649 | B1 | 10/2014 | Rao et al. |
| 9,125,798 | B2 | 9/2015 | Stein et al. |
| 9,358,183 | B2 | 6/2016 | Stein et al. |
| 10,433,666 | B1 | 10/2019 | Jovanov et al. |
| 2004/0215521 | A1 | 10/2004 | Crisp, III |
| 2005/0215915 | A1 | 9/2005 | Noda |
| 2008/0039700 | A1* | 2/2008 | Drinan ............... A61B 5/6887 600/301 |
| 2011/0224529 | A1 | 9/2011 | Lading |
| 2013/0066168 | A1 | 3/2013 | Yang |
| 2013/0211208 | A1 | 8/2013 | Varadon et al. |
| 2014/0221849 | A1* | 8/2014 | Farringdon ............ A61B 5/30 600/483 |
| 2015/0282768 | A1 | 10/2015 | Luna |
| 2016/0007935 | A1 | 1/2016 | Hernandez |
| 2016/0220184 | A1 | 8/2016 | Manion |
| 2018/0055455 | A1 | 3/2018 | Hu |

FOREIGN PATENT DOCUMENTS

| | | |
|---|---|---|
| WO | 2007057014 A1 | 5/2007 |
| WO | 2013186688 A1 | 12/2013 |

OTHER PUBLICATIONS

Brüser, et al., "Ambient and Unobtrusive Cardiorespiratory Monitoring Techniques," IEEE Reviews in Biomedical Engineering, Jan. 2014, 18 pages.

Jovanov, et al., "Smartstuff: A Case Study of a Smart Water Bottle," 38th Annual International of the IEEE Engineering in Medicine and Biology Society, Aug. 2016, 4 pages.

Marasco, et al., "A Survey on Anti-Spoofing Schemes for Fingerprint Recognition Systems," ACM Computing Surveys, Sep. 2014, 36 pages, vol. 47, No. 2, Article A.

Ding, et al., "A Comprehensive Survey on Pose-Invariant Face Recognition," ACM Transactions on Intelligent Systems and Technology, Mar. 2016, 40 pages, vol. 7, Issue 3.

Jovanov, et al., "Design and Feasibility of a Safe Pill Bottle," Applied System Innovation, 2018, 11 pages, vol. 1.

Talukder, et al., "A New Method to Prevent Unintentional Child Poisoning," 40th Annual International Conference of the IEEE Engineering in Medicine and Biology Society, Jul. 2018, 4 pages.

Brotfain, et al., "Urine Flow Rate Monitoring in Hypovolemic Multiple Trauma Patients," World Journal of Emergency Surgery, 2017, 6 pages.

Garrett, et al., "Engineering Approaches to Assessing Hydration Status," IEEE Reviews in Biomedical Engineering, 2018, pp. 233-248, vol. 11.

Majumder, et al., "Noncontact Wearable Wireless ECG Systems for Long-Term Monitoring," IEEE Reviews in Biomedical Engineering, 2018, pp. 306-321, vol. 11.

Hersch, et al., "Accuracy and Ease of Use of a Novel Electronic Urine Output Monitoring Device Compared with Standard Manual Urinometer in the Intensive Care Unit," Journal of Critical Care, 2009, pp. 629.e13-629.e17, vol. 24.

Deurenberg, et al., "Multi-Frequency Impedance for the Prediction of Extracellular Water and Total Body Water," British Journal of Nutrition, 1995, pp. 349-358, vol. 73.

Armstrong, "Assessing Hydration Status: The Elusive Gold Standard," Journal of the American College of Nutrition, 2007, pp. 575S-584S, vol. 26, No. 5.

"Acute Kidney Injury (AKI)," National Kidney Foundation, https://kidney.org/atoz/content/AcuteKidneyInjury, pp. 1-3.

Premanode, et al., "A Novel, Low Power Biosensor for Real Time Monitoring of Creatinine and Urea in Peritoneal Dialysis," NSTI-Nanotech, 2006, pp. 221-224, vol. 2.

Li, et al., "A Large-Scale Measurement of Dielectric Properties of Normal and Malignant Colorectal Tissues Obtained from Cancer Surgeries at Larmor Frequencies," Medical Physics Nov. 2016, pp. 5791-5597, vol. 43 No. 11.

Ezerskaia, etaL, "Quantitative and Simultaneous Non-lnvasive Measurement of Skin Hydration and Sebum Levels," Biomedical Optics Express, Jun. 2016, 10 pages, vol. 7, No. 6.

Jovanov, et al., U.S. Appl. No. 16/174,163, entitled, "Systems and Methods for Monitoring Physiological Parameters with Capacitive Sensing," filed Oct. 29, 2018.

Emil Jovanov, "Vital Sign Monitoring Using Capacttive Sensing," 40th Annual International Conference of the IEEE Engineering in Medicine and Biology Society, Jul. 2018, 4 pages.

Ramezani, "An Implementation of Embedded Software for Real Time Monitoring of Bioimpedance," The University of Alabama in Huntsville, Dec. 16, 2020, pp. 1-91.

* cited by examiner

SYSTEMS AND METHODS FOR MONITORING HYDRATION

CROSS REFERENCE TO RELATED APPLICATIONS

This application claims the benefit of U.S. Provisional Application No. 62/981,894, entitled "Seamless Hydration Monitoring System" filed on Feb. 26, 2020. This application is also a continuation-in-part of U.S. patent application Ser. No. 16/174,163, entitled "Systems and Methods for Monitoring Physiological Parameters with Capacitive Sensing," and filed on Oct. 29, 2018, which application claims the benefit of U.S. Provisional Application No. 62/578,209, entitled "A System and Method for Physiological Monitoring of Users Using Capacitive Sensing" filed on Oct. 27, 2017. U.S. patent application Ser. No. 16/174,163 also is a continuation-in-part of U.S. patent application Ser. No. 15/239,810, entitled "Liquid Container Systems and Methods for Monitoring User Hydration," and filed on Aug. 17, 2016 and granted as U.S. Pat. No. 10,433,666, which application claims priority to U.S. Provisional Application No. 62/205,839, entitled "Systems and Methods for Monitoring Liquids in a Container" filed on Aug. 17, 2015, U.S. Provisional Application No. 62/241,494, entitled "Systems and Methods for Monitoring Liquids in a Container" filed on Oct. 14, 2015, and U.S. Provisional Application No. 62/330,692, entitled "Smart Bottle Systems and Methods" filed on May 2, 2016. All of the previously listed applications are incorporated herein by reference.

BACKGROUND

The present disclosure relates to systems and methods for monitoring user hydration during interaction with objects of everyday use.

Assessment of the hydration status of a person is very important for a number of health conditions. Dehydration is common in hospitals and care homes and associated with poorer outcomes. It is estimated that dehydration is a trigger for almost half of hospital admissions of the elderly. Dehydration is under-recognized and poorly managed in hospital and community-based care.

The precise assessment of the hydration status of a person using a single measurement is very hard, even in laboratory settings. This is primarily due to the complex physiological dynamics of fluid management in the body. Few assessment methods have been validated to accurately measure the fluid compartments in the body, but they have little application in practice. Different techniques have been developed to determine hydration status for the user in clinical settings, but their diagnostic accuracy remains questionable.

Hydration status has been correlated with the performance of athletes and with mental performance. An abnormal hydration status includes relative and/or absolute abnormalities in body water and serum/plasma osmolality (pOsm). A raised pOsm usually indicates dehydration and a direct measurement of pOsm can be used to determine a dehydration level in a person. For example, a person having a pOsm >300 or ≤280 mOsm/kg classifies a person as either hyper or hypo-osmolar.

Bioimpedance-based methods have been used for assessment of Total Body Water (TBW) and Extra Cellular Water (ECW) in persons for more than 30 years. Some methods of determining TBW or ECW use complex impedance parameters, such as reactance and phase angle. Several methods use the sex, height and weight of the user for assessing TBW or ECW. Typical frequencies used in the analysis are 5 KHz and 100 KHz, in some cases the frequencies used can be as low as 1 KHz or in range of 10-50 KHz. There are no commercially available devices for real-time assessment of hydration status. Several devices, including smart weight scales, assess TBW and ECW using whole body bioimpedance measured through the feet, but require the person to be continuously using the scale with bare feet to determine TBW and ECW. Clinical grade bioimpedance-based devices use a whole body measurement. Typically, the clinical devices use 4 special electrodes that are applied to legs and arms during measurement, a pair for stimulation and a pair for signal acquisition. However, such an arrangement would impact a person's ability to conduct everyday activities. Thus, it would be beneficial to monitor hydration status directly using unobtrusive sensors on objects of everyday use.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

Figure 1:
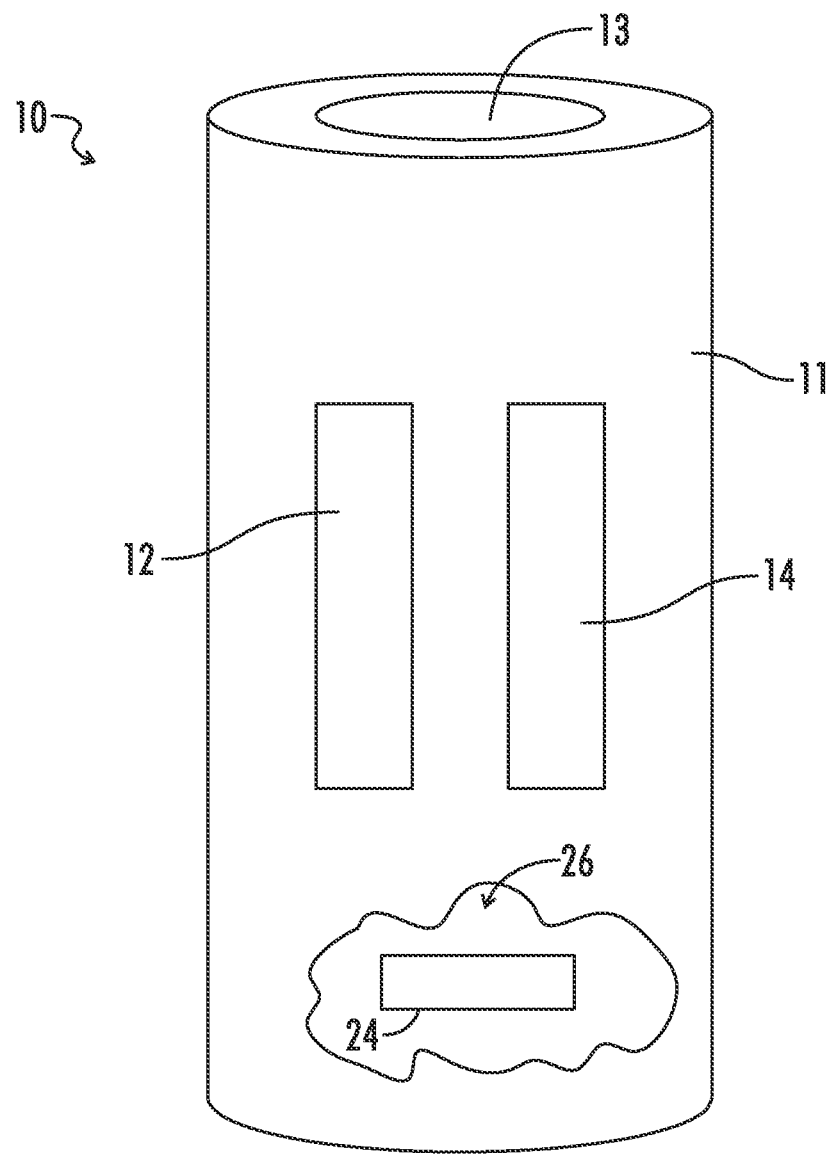
FIG. 1 shows a perspective view of an embodiment of a smart container.

The present disclosure generally pertains to smart objects for use in monitoring user hydration and/or monitoring physiological parameters of a user. In one exemplary embodiment, a smart beverage container has an interior volume that is capable of holding a volume of a liquid. The smart container also comprises at least one sensor for sensing an amount of the liquid within the container. The liquid is monitored over time to determine an amount of liquid consumed by a user, and feedback is provided to the user indicating whether the user's liquid consumption is within a desired range. Such feedback may include information for indicating when the user is to consume additional liquid in order to remain in compliance with a desired liquid consumption regimen or at a desired hydration level or warn the user if too much liquid had been consumed. More generally, the smart container can be used to monitor the consumption or use of any liquid stored in the smart container. Alternatively, the smart container can monitor the level of a liquid being stored or captured by the smart container.

In one embodiment, the amount of liquid in the container is measured by at least one capacitive sensor fixedly located at one or more locations of the container. The capacitive sensor is configured to provide a capacitive signal representative of the volume of liquid in the container, or a section of the container. The smart container can also have at least two additional impedance sensors fixedly located on the exterior of the contained and positioned to contact the skin of the user when the user grasps the container. The additional impedance sensors can be used to determine the hydration level of the person. The smart container can include a controller fixedly attached to the container. The controller of the smart container can include a memory, a clock, control logic, and a communication interface. The control logic is configured to receive the capacitive signal, the additional impedance data, and a clock signal from the clock, and is configured to determine liquid information data (such as the level of the liquid, the volume of the liquid and the rate at which the level or volume is increasing or decreasing) and the hydration level of the user based on one or more of the capacitive signals, the additional impedance data, and the clock signal. The control logic is also configured to store the liquid information data and the hydration level in the memory and provide at least a portion of the liquid information data and hydration level to the communication interface. The communication interface is configured to communicate with an electronic device, such as a smartphone or a remote server via a wireless communication link (e.g., a router), and to transmit the liquid information data and the hydration level to the electronic device or the remote server.

In one embodiment, the communication interface is also configured to receive one or more warnings or indications from the electronic device or the remote server. The control logic is configured to provide the one or more warnings or indications to the user interface, and the user interface is configured to display the one or more warnings or indications to the user.

In one embodiment, the control logic is configured to generate one or more warnings or indications based on the liquid information data and the hydration level and to provide the one or more warnings or indications to the user interface. The user interface is configured to display the one or more warnings or indications. As an example, the control logic may be configured to track the hydration of the user or the consumption of the liquid in a beverage container over time based on at least one parameter indicative of an amount of liquid in the beverage container. If the amount of liquid consumed or the hydration level of the person during a time period is inconsistent with a target hydration profile throughout the day (e.g., more or less than a desired amount to be consumed or more or less than a desired hydration level during the day) for the user, the control logic may be configured to initiate a warning, which is displayed by the user interface. Such warning may be in the form of a text message, notification, or some other format. As an example, the user interface may comprise one or more light sources (e.g., light emitting diodes) that are illuminated as a warning that too much or too little liquid has been consumed. In other examples, other types of warnings, such as audio beeps or spoken messages, may be provided.

In another embodiment, a smart object can include similar components to the smart container but can use a capacitive or optical sensor to measure a physiological parameter, such as heart rate or blood pressure, of a user. The capacitive sensor can be located on the exterior of the object and measure a capacitance associated with the user coming into contact with the capacitive sensor. The measured capacitance, or more specifically, the changes in capacitance, can then be used to determine the desired physiological parameters of the user. For example, a user's heartbeat can be detected by detecting corresponding changes in capacitance measured by a capacitive sensor that is being touched by the user. In an embodiment, the smart container may also have exterior capacitive sensors and operate similar to the smart object to provide physiological information on the user of the smart container.

FIG. 1 shows a perspective view of smart object 10 configured as a smart container. Smart object 10 includes at least one container 11 for holding a beverage. Container 11 may be any suitable container that may hold a consumable liquid, such as a cup, bottle, water bottle, sports bottle, baby bottle or any other known beverage or consumable liquid container. As shown in FIG. 1, container 11 includes a bottom, a cylindrical side, and an opening 13. Although container 11 is depicted in this manner, it will be understood that container 11 may be any suitable object that is able to contain a liquid and selectively provide a user with access to a liquid (e.g., through an opening).

Also shown schematically in FIG. 1 are user interface 12 and sensors 14. In the embodiment of FIG. 1, user interface 12 and sensors 14 are depicted as attached to an external surface of container 11. It will be understood that user interface 12 and sensors 14 may be provided for the smart object 10 at any suitable location, including being integrally formed with container 11. User interface 12 may allow a user to interact with smart object 10, as described in more detail hereafter. User interface 12 may provide information about smart object 10, such as environmental information, information relating to a liquid in container 11, information relating to a user of smart object 10, any other suitable information, or any combination thereof.

The smart container 10 may also include a capacitive sensor 20 (see FIG. 2) that can be used to determine the amount of liquid in the container 11. Additional information regarding the operation of the capacitive sensor 20 can be found in U.S. Pat. No. 10,433,666 entitled "Liquid Container Systems and Methods for Monitoring User Hydration" and in U.S. patent application Ser. No. 16/174,163, entitled "Systems and Methods for Monitoring Physiological Parameters with Capacitive Sensing," both of which are incorporated by reference herein.

Also depicted in FIG. 1 is a cavity 26. Located within cavity 26 is a controller 24. As will be described in more detail herein, controller 24 may receive inputs from sensors 14 and capacitive sensor 20, may interact with user interface 12, and may communicate with other devices such as other smart objects 10 or electronic devices 70 (e.g., smartphones, tablets, smart watches, personal computers, etc.). Although controller 24 is depicted as located within cavity 26, it will be understood that controller 24 may be located at any suitable location of smart object 10. For example, controller 24 may be located integrally within container 11 of smart object 10, on an exterior surface of container 11, on an interior surface of container 11, or in any other suitable location. Whether or not controller 24 is located within cavity 26, it will also be understood that controller 24 need not be located at a bottom or base of container 11, but may be located at any suitable location of container 11.

Figure 2:
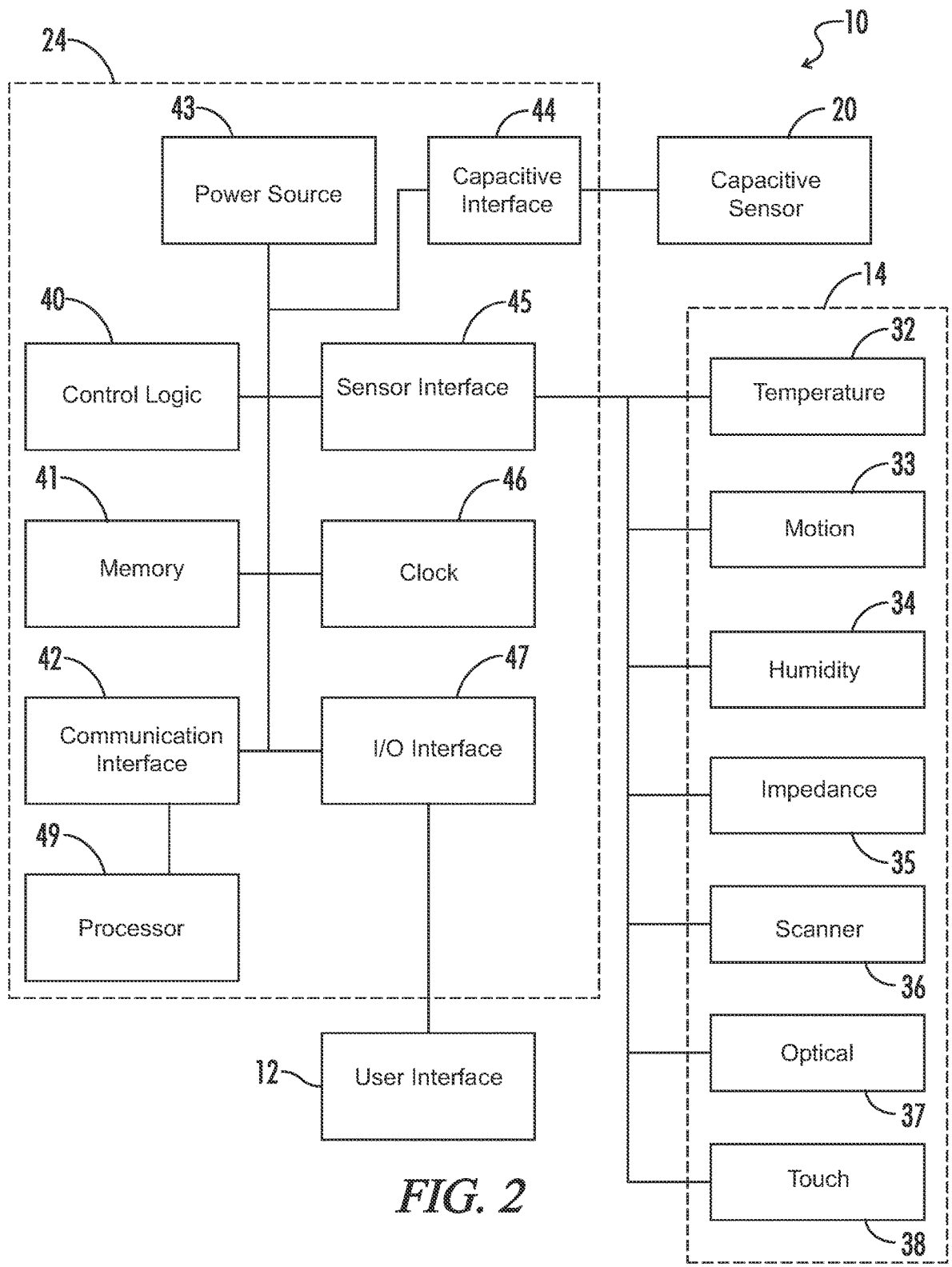
FIG. 2 shows a block diagram of an embodiment of a controller, capacitive sensor, additional sensors, and user interface of a smart container.

FIG. 2 is a block diagram of an embodiment of controller 24, capacitive sensor 20, additional sensors 14, and user interface 12 of smart object 10. Controller 24 may monitor capacitive sensor 20 and sensors 14 and may also facilitate communication with the user of smart object 10 through user interface 12. Capacitive sensor 20 may include any suitable arrangement of electrodes that permit capacitive sensing of the volume of container 11 that includes the liquid.

FIG. 2 depicts a number of additional sensors 14 including a temperature sensor(s) 32, motion sensor(s) 33, humidity sensor(s) 34, complex impedance sensor(s) 35, scanner 36, optical sensor(s) 37 (e.g., a photoplethysmographic (PPG) sensor), touch sensor(s) 38 and/or combinations thereof. Although particular sensors are depicted in FIG. 2, controller 24 may receive sensor information from any suitable sensor 14. Suitable sensors may include sensors that are able to determine information about a liquid within container 11, sensors that are able to determine information relating to the environment in which the smart object 10 is being used, and sensors that are able to determine information about a user of smart object 10. Thus, while particular sensors are described for use in certain applications, it will be understood that any suitable sensors may be used for any suitable applications.

In one embodiment, a temperature sensor 32 may measure the temperature of a liquid within smart object 10, an exterior temperature (e.g., ambient air temperature), or both. A temperature of the liquid may be used for numerous applications. In one exemplary application, the temperature may be used to determine whether a liquid is suitable for drinking, for example, if a liquid is too hot to be consumed. In another embodiment, the type of liquid may be known such that it is known that certain temperatures or humidity levels are likely to result in spoilage of the liquid over time. For example, dairy products exposed to high temperatures for an extended period may be likely to spoil. If the container 11 is a baby bottle, the temperature sensor 32 can be used to determine whether the liquid in the container 11 is at a temperature that may injure an infant that drinks from the container 11 and the humidity sensor 34 may be used with temperature sensor 32 to determine if the contents of the container 11 may have spoiled, which may also injure an infant that drinks from the container 11. In other embodiments, temperature information may be used to optimize consumption of the liquid. For example, it may be desirable to consume certain liquids within a particular temperature range for the liquid. Based on information from temperature sensor 32, controller 24 may determine whether the liquid is within the desired temperature range. In other embodiments, temperature sensor 32 may be used to determine when the type of liquid within smart object 10 has changed. For example, a change in the temperature that is sensed by temperature sensor 32 over a short time period may indicate that the type or volume of liquid inside smart object 10 has changed. This information can be used to indicate an optimum temperature of the liquid for the user (e.g., temperature of the baby food with predefined tolerance of temperature). When the controller 24 determines that the liquid is unsuitable for consumption (e.g., the temperature has been above a threshold for a sufficient amount of time to indicate that spoilage is likely or the temperature is otherwise outside of a desired range for consumption), the controller 24 may be configured to initiate a warning, such as a textual or graphical warning message to be viewed by the user.

In one embodiment, the controller 24 receives an input indicating the type of liquid that is in the container 11. Further, memory 41 stores data indicative of a desired temperature range associated with the liquid type. If the measured temperature is outside of the desired range, then the controller 24 may provide a warning via the user interface 12 or otherwise. Note that the data may be temporal in nature. For example, the data may indicate that a warning is to be generated if the temperature is within a specified range for at least a specified amount of time. In such case, the controller 24 determines how long, based on clock 46, the temperature is within the indicated range (e.g., above a temperature threshold), and generates a warning if the cumulative time is above a predefined time threshold.

A temperature sensor 32 may also measure temperature information relating to the environment in which smart object 10 is used. An environmental temperature measurement may be used to optimize the consumption of a liquid within smart object 10. In one embodiment, controller 24 may provide indications to user interface 12 for a user to increase or decrease the rate at which they are consuming a liquid based on a sensed environmental temperature. As an example, when ambient air temperature is above a predefined threshold, the controller 24 may increase the amount of liquid that is to be consumed over a given time period in an attempt to ensure that the user remains sufficiently hydrated in elevated temperature conditions.

In some embodiments, sensors 14 of smart object 10 may include one or more motion sensors 33. Motion sensors 33 may include any suitable motion sensor such as accelerometers, gyroscopes, magnetometers, proximity sensors, any other suitable sensor, or any combination thereof. Motion sensors 33 may provide information that is useful in determining the optimum consumption of liquid within smart object 10. In one embodiment, information from motion sensors 33 may be used to determine when a user is consuming liquid from smart object 10. Such information may be used for numerous purposes, such as determining the rate of which a user is consuming a liquid. For example, information about when a user is consuming a liquid as determined from motion sensors 33 may be used on combination with information about the volume of liquid in smart object 10 (e.g., from capacitive sensor 20) and clock 46 to determine the rate at which a user is consuming the liquid. In another embodiment, information from motion sensors 33 may be used to determine an appropriate time to consume a liquid within smart object 10. For example, when smart object 10 is experiencing a large amount of motion, it may not be desirable to consume a liquid within smart object 10. Such information may also be combined with information from other sensors (e.g., temperature sensor 32) to determine when it is appropriate to consume a liquid (e.g., for consumption of hot liquids). Pattern of motion in time (e.g., orientation of the container) may be used to characterize the use of the container, or identify the user. In another embodiment, the relative angle of the container 11 calculated from the inertial sensor can be used to assess the amount of liquid in the container 11, the rate of the consumption by the user, or to improve the accuracy of the assessment of the volume of liquid and/or consumption rate.

In one embodiment, motion sensors 33 may be used to provide a wake up signal for the electronics of smart object 10. When a motion sensor 33 (e.g., a gyroscope or accelerometer sensing motion, or a proximity sensor sensing presence) senses that the smart object 10 is being used, a signal may be provided to controller 24. Prior to the signal being provided, the components of smart object 10 may be in a sleep mode or low sampling rate to limit power consumption. In response to the motion sensors 33 identifying the use of smart object 10, the components of smart object 10 may wake up and operate normally or increase the sampling rate.

Sensors 14 may also include one or more humidity sensors 34. In one embodiment, humidity sensor 34 may measure the humidity of the environment in which smart object 10 is being used. Depending on the type of liquid that is being consumed, it may be desirable to change the rate at which the liquid is consumed, for example to increase the consumption rate if the humidity is high. In some embodiments, it may be desirable to discard a liquid if it is located in a high humidity environment over an extended period of time (e.g., due to spoilage). In some embodiments, a value for liquid volume data may be adjusted based on the humidity and/or temperature. An initial liquid volume value may be determined based on the measurement from the capacitive sensor. That initial liquid volume data may be adjusted based on known characteristics of the liquid in response to temperature or humidity.

Sensors 14 may also include impedance sensor 35. Although an impedance sensor 35 may be implemented in any suitable manner, in one embodiment an impedance sensor 35 may include a plurality of electrodes that provide a waveform signal at a certain frequency or combination of frequencies and that is transmitted through the liquid of smart object 10. Based on the changes in the amplitude and phase of the waveform signal, characteristics of the liquid within smart object 10 may be determined. In this manner, impedance sensor 35 operating in conjunction with controller 24 may be able to identify and distinguish between liquids based on a known profile of the liquid or may be able to identify a nutritional content of liquids (e.g., sugar, fat, carbohydrate, calories, and salt content). Such information may be used for monitoring applications as are described hereafter.

As an example, information indicating the capacitance and impedance ranges for a plurality of liquids may be stored in the memory 41. The controller 24 may be configured to compare such information to the measured capacitance and impedance of the liquid in order to identify the type of liquid that is currently in the object 10. Based on such liquid type, the controller 24 can determine nutritional information, such as caloric intake or the intake of certain substances (e.g., sugars or carbohydrates), of the consumer liquid. The feedback provided to the user may include such nutritional information as may be desired. In addition, the liquid type information may be used by the controller 24 to determine the desired range of consumption. As an example, the controller 24 might target a higher consumption amount for water relative to sports energy drinks.

In another embodiment, the impedance sensor 35 and corresponding electrodes or contacts may be located on the exterior of smart object 10 and measure a complex impedance (including real and imaginary components) associated with a user holding or touching the smart object 10. The impedance sensor 35 can operate like a hydration sensor and determine the total body water (TBW), total body water percentage (TBW %) or extra cellular water (ECW) of the user from the measured complex impedance. The determined TBW, TBW % or ECW can then be used to determine a dehydration or lack of hydration level associated with the user. The impedance sensor 35 can emit signals (e.g., a current source as a sine wave) of different frequencies at a first electrode (stimulating electrode). The signals flow through the hand (or body) of the user and are then detected at a second electrode (sensing electrode). The impedance sensor 35 can include an amplifier to amplify the detected signals at the second electrode, or an integrated network analyzer for bioelectrical impedance analysis (e.g., Texas Instruments AFE4300 or Analog Devices AD5933). In an embodiment, the complex impedance can be measured at 1 KHz, 5 KHz, 50 KHz and 100 KHz. The measured complex impedances can then be used to assess the relative change of hydration level of the user based on a formula that is personalized to the user (e.g., accounts for the height and weight of the user). In an embodiment, the impedance sensor 35 can incorporate 2 (or more) first electrodes and 2 (or more) second electrodes to measure complex impedance.

Sensors 14 may also include an osmotic sensor (not shown) and a scanner 36. The osmotic sensor can be implemented in a spout of the container 11 to measure the hydration level of the user and is connected to controller 24 via sensor interface 45. Scanner 36 may be any suitable device that may determine a type of liquid based on identifying information such as a liquid label. In one embodiment, scanner 36 may be a barcode or QR code scanner. In this manner, information relating to a liquid that is placed inside smart object 10 may be ascertained. Scanner 36 may provide the bar code or QR code information to controller 24, which may have corresponding nutritional information in a memory or may acquire such information by communicating with an external computing device or server. This information may be used along with information from capacitive sensor 20 or other sensors 14 for purposes such as caloric or nutritional monitoring.

The optical sensor 37 can be used to measure physiological parameters such as heart rate, blood oxygen saturation (SpO2), and/or any other corresponding physiological parameter. In an embodiment, the optical sensor 37 can be integrated into the exterior of the object 10. With the integration of the optical sensor 37 into the exterior of the object 10, each time the object 10 is handled or touched by a user (e.g., to consume a liquid), the optical sensor 37 can be used to measure the user's heart rate and/or blood oxygen saturation. The optical sensor 37 can then provide data indicative of such measurement(s) to controller 24 for subsequent monitoring of the measurements and/or other related parameters.

Figure 4:
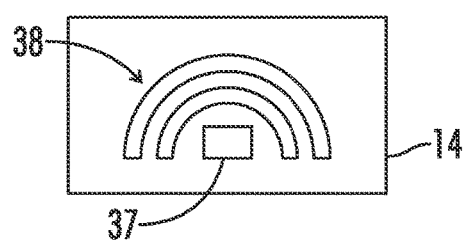
FIG. 4 shows an embodiment of a sensor incorporating an optical sensor and a capacitive touch sensor.

Touch sensor 38 can be used to detect handling or touching of object 10 and/or other parameters (including physiological parameters of the user). The touch sensor 38 can be integrated into the exterior of the object 10 and can include a capacitive sensor. In an embodiment, as shown in FIG. 4, sensor 14 can incorporate both a touch sensor 38 and an optical sensor 37. The touch sensor 38 in FIG. 4 can be used to detect touching or contacting of the object 10 such that a determination can be made as to when the object 10 is being handled or used and to activate or "turn on" the optical sensor 37 only when the object 10 is being used, thereby significantly reducing power consumption of the optical sensor 37. In another embodiment, changes of capacitance detected by touch sensor 38 can be combined with measurements from optical sensor 37 to provide a more robust measurement of heart rate. In another embodiment, a low frequency sampling of reflected light on the optical sensor 38 may be used to detect contact with the object 10.

The sensor 14 shown in FIG. 4 can include a printed circuit board (PCB) having dimensions of about 0.625 inches by about 0.920 inches. In an embodiment, the optical sensor 37 can be from the Maxim MAX310X family of heart rate and pulse oximeter sensors having dimensions of about 5.6 mm and 2.8 mm and can include two light emitting diodes (LEDs), a photodetector, optimized optics and low-noise analog signal processing. The sensor 14 can include a power management circuit (not shown) that can be positioned on the bottom of the PCB for use with both 1.8 V and 3.3. V power supplies. The controller 24 can communicate with the optical sensor 37 via I2C. The controller 24 can provide instructions to the optical sensor 37 directed to low power mode control, FIFO control, LED power usage and temperature measurement control. The optical sensor 37 can provide a raw PPG signal to the controller 24 that can then digitize the PPG signal. The top layer of the PCB can include a capacitive sensor for touch sensor 38.

Referring back to FIG. 2, smart object 10 also includes a user interface 12. User interface 12 may vary in complexity from a simple user interface to a complex user interface. As an example of a simple user interface, a user interface 12 may include a series of LEDs (e.g., red, yellow, and green LEDs or a single, multicolor, LED) and a plurality of buttons that can include one or more capacitive touch buttons. LEDs may be used to communicate various types of information, such as a hydration level for a user. A plurality of buttons may be used to input simple information such as selecting between one of several options. In some embodiments, user interface 12 may be a complex user interface. Although a complex user interface may be implemented in any suitable manner, an example of a complex user interface may be a touch screen interface. A touch screen interface may allow complex interface information to be displayed to the user and may allow the user to input data (e.g., information relating to the height or weight of the user) or otherwise interact with a visual display in a complex manner. In other embodiments, user interface 12 may be implemented in any gradation between a simple user interface and a complex user interface. In some embodiments, user interface 12 may include one or more non-visual user interface types. For example, user interface 12 may include a speaker and microphone that operate in conjunction with speech recognition to allow the user to interact with the smart object 10 through voice commands or receive spoken recommendations and notifications.

In some embodiments, user interface 12 may include a biometric interface. A biometric interface may include any suitable components or device that assists in the identification of a particular user of smart object 10. In one embodiment, a fingerprint scanner may be used to identify a user. In other embodiments, a camera may be used to capture images that may be used for facial or iris recognition. Identifying a user (which also may be done through a voice recognition interface) may be useful to associate the user with liquid consumption for operation of a monitoring program.

Smart object 10 also includes a controller 24. Although controller 24 may include any suitable components, in one embodiment controller 24 includes processor 49, control logic 40, memory 41, communication interface 42, power source 43, capacitive interface 44, sensor interface 45, clock 46, and I/O interface 47. In the embodiment described herein, controller 24 interfaces with capacitive sensor 20, sensors 14, and user interface 12 to determine hydration and physiological data and provides that hydration and physiological data to an electronic device 70 via communication interface 42. Thus, control logic 40 of controller 24 performs calculations to determine the hydration and physiological data from the received sensor and user interface information. However, it will be understood that in some embodiments control logic 40 of controller 24 may perform additional monitoring applications based on the calculated hydration and physiological data (e.g., blood pressure) or that control logic 40 of controller 24 may perform fewer processing functions (e.g., transmitting the received sensor and user information to an electronic device 70 for the hydration and physiological data to be determined elsewhere).

Although control logic 40 may be implemented in hardware, software, or any suitable combination thereof, in one embodiment control logic 40 may include one or more processors (e.g., processor 49) having processing capability necessary to perform the processing functions described herein, including but not limited to hardware logic, computer readable instructions running on one or more processors, or any suitable combination thereof. In an embodiment, control logic 40 may have at least one processor for running software to perform the operations described herein, including software accessed in machine readable form on a tangible non-transitory computer readable storage medium, as well as software that describes the configuration of hardware such as hardware description language (HDL) software used for designing chips. In some embodiments, the processor may include a general- or special-purpose microprocessor, finite state machine, controller, computer, central-processing unit (CPU), field-programmable gate array (FPGA), application specific integrated circuit (ASIC), or digital signal processor.

Control logic 40 is in communication with each of the components of controller 24 and controls the operation of smart object 10 through the components of controller 24. Through interfaces of controller 24, control logic 40 is able to control sensors and read sensor data, communicate with a user via user interface 12, and communicate with other electronic devices via communication interface 42. Through operational circuitry of controller 24 (e.g., memory 41, power source 43, and clock 46) control logic 40 is able to control the operation of components of controller 24 and read and access stored information.

Controller 24 includes memory 41, which may be a tangible storage medium. Examples of tangible (or non-transitory) storage medium include disks, thumb drives, and other forms of memory. Tangible computer readable storage medium include volatile and non-volatile, removable and non-removable media, such as computer readable instructions, data structures, program modules or other data. Examples of such media include RAM, ROM, EPROM, EEPROM, flash memory, disks or optical storage, magnetic storage, or any other non-transitory medium that stores information that is accessed by a processor or computing device. In some embodiments (not depicted), one or more computer readable storage media may be integrated with control logic 40, may be one or more other components of controller 24, may be located on another device, may be located at a remote location, or any combination thereof.

In one embodiment, memory 41 may store information including operational data, user data, sensor data, and liquid information data. Operational data may include any suitable data for operating smart object 10 and any components thereof. Operational data may include instructions that execute on the processor 49 of control logic 40 for operating smart object 10. Operational data may also include information relating to the operation of the components of smart object 10, such as communication protocols or information for communication interface 42, control information for power source 43, scaling and control information for capacitive sensor interface 44 and sensor interface 45, control information for clock 46, and information relating to the available input and output options for user interface 12 (via I/O interface 47). User data may include any suitable information relating to a user, such as identifying information (e.g., name, age, gender, weight, and height), stored user records (e.g., a history of hydration and physiological information), sensor data (e.g., raw sensor data captured from capacitive sensor 20 or sensors 14), and hydration and physiological data (e.g., calculated TBW or ECW).

Controller 24 also includes a communication interface 42. Communication interface 42 may be a wired interface, wireless interface, or any combination thereof. A wired interface of communication interface 42 may include a receptacle to interface with a wired connection and communication circuitry for sending and receiving data over a suitable wired connection (e.g., Ethernet, USB, FireWire, lightning, etc.). A wireless interface of communication interface 42 may include a wireless transceiver and related circuitry for transmitting and receiving data over any suitable wireless interface (e.g., Wi-Fi, Bluetooth, cellular, NFC, etc.). In some embodiments, communication interface 42 may also include processing circuitry for communicating high level data and commands with control logic 40, or in some embodiments, such processing circuitry may be integral to control logic 40.

Controller 24 also includes a power source 43. In one embodiment, power source 43 may include a battery such as a lithium-ion battery, lithium-polymer battery, nickel-cadmium battery, or nickel-metal-hydride battery. Power source 43 may include a charging interface such as a physical connector to attach to a charger or wireless inductive charging circuitry. Power source 43 may also include control circuitry that allows the charging and output power of the power supply 43 to be controlled (e.g., by control logic 40).

Controller 24 may also include capacitive sensor interface 44. Capacitive sensor interface 44 may interface with control logic 40, such that control logic 40 may control operational parameters of capacitive sensor 20 (e.g., potential) and receive sensed capacitance values from capacitive sensor 20. Capacitive interface 44 may communicate these sensed capacitance values to control logic 40 as raw values in analog or digital form, or as a data signal that communicates the capacitance value.

Controller 24 also includes sensor interface 45. Although a single sensor interface 45 is depicted, in some embodiments a separate sensor interface 45 may be included for each of the sensors 14. Sensor interface 45 is able to communicate with control logic 40 in order to control the operation of sensors 14 and provide sensor data (e.g., temperature sensor data, motion sensor data, humidity sensor data, impedance sensor data, scanner sensor data, etc.) to control logic 40. Sensor interface 45 may provide the sensor data to control logic 40 in raw form as an analog or digital signal or via a data signal that includes the sensor data.

Controller 24 also includes a clock 46. Clock 46 may be any suitable device that provides a clock signal for controller 24. In some embodiments, clock 46 may provide a plurality of clock outputs or may have a plurality of modes to enable different clock rates. Clock 46 provides a clocking signal for control logic 40 and may also be used to provide other timing references for components of smart object 10.

Controller 24 also includes an I/O interface 47. I/O interface 47 may allow control logic 40 to control the operation and display of user interface 12 and receive user input via user interface 12. I/O interface 47 may include any suitable circuitry based on the type of user interface 12. In one embodiment of user interface 12 including LEDs and buttons, I/O interface 47 may include circuitry for driving the LEDs and for providing electrical signals in response to interaction with the buttons. In one embodiment of a touch screen, I/O interface 47 may include processing and driver circuitry for controlling a display of the touch screen and receiving touch inputs from the touch screen. In one embodiment of an audio and voice interface 12, I/O interface 47 may include circuitry for providing and receiving electrical signals representative of voice or other audio information, and may include circuitry for providing electrical or data signals representing voice or audio information to control logic 40.

Figure 3:
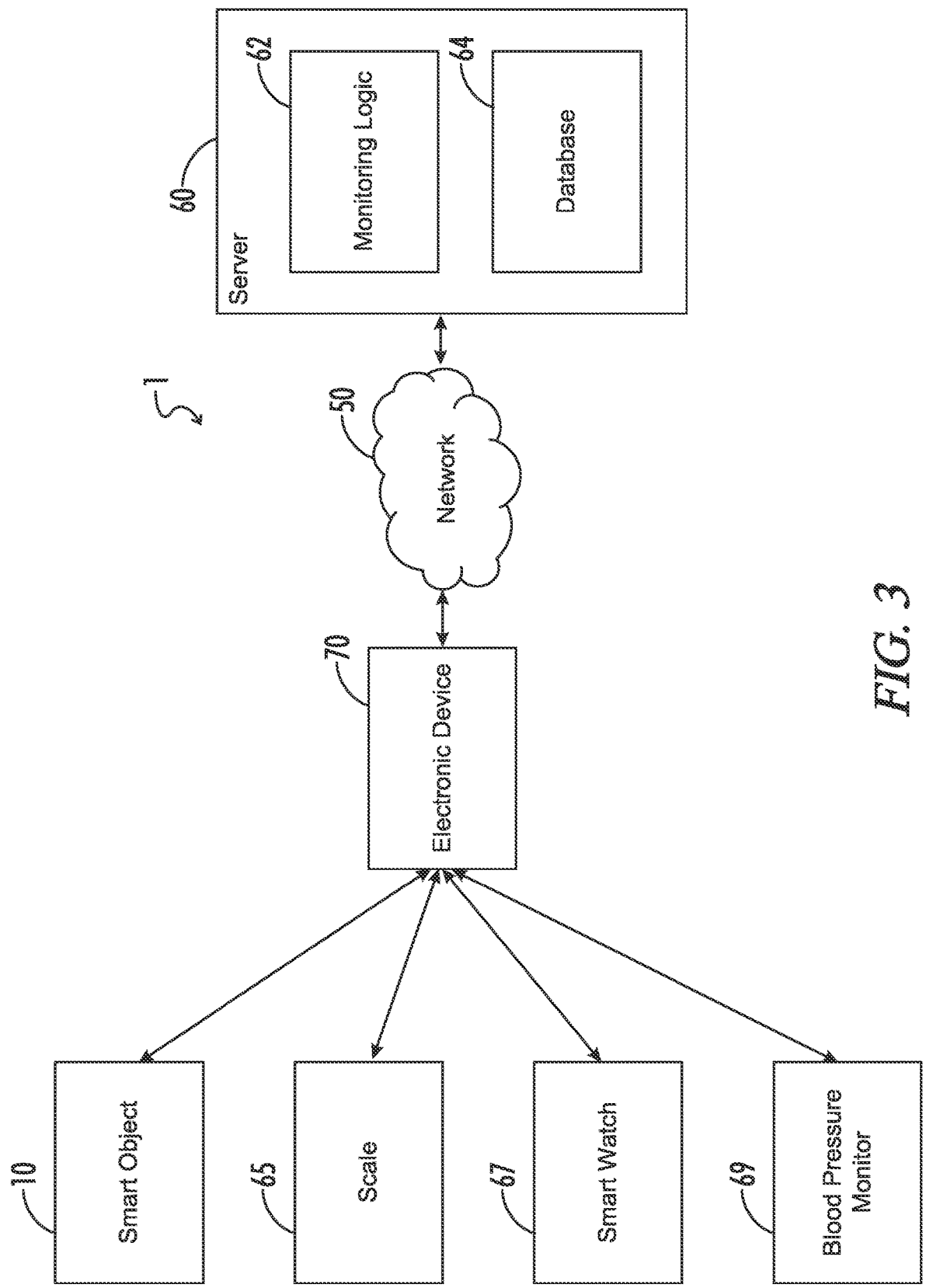
FIG. 3 shows an embodiment of a monitoring system.

FIG. 3 shows an embodiment of monitoring system 1 including a smart object 10, other smart devices (e.g., a body composition scale 65, a smart watch 67 and/or a blood pressure monitor 69), electronic device 70, and server 60. The server 60 may be located at the home of the person in one embodiment to store the person's personal information, but the server 60 could be located remote from the user and be associated with a hospital, nursing home or other medical facility. In addition, a server 60 located at the person's home may also communicate via the Internet with a remote medical server at a hospital, nursing home or other medical facility.

In an embodiment, the smart body composition scale 65 can be used to automatically update the weight of the user in the personal medical record of the user stored in database 64. The body composition scale 65 may also provide a whole body bioimpedance measurement through the bare feet of the user that can be used as an independent measure of the hydration level of the user. The controller for the body composition scale 65 may also use scanning of wireless devices to identify the user (e.g., the determination of an RSSI of a personal badge or a personal device (e.g. a smart watch) of the user). The measurements from the scale 65 can be uploaded on the server 60 through network 50.

In addition, the providing of hydration measurements and other information (e.g., weight) from the body composition scale 65 (or from a clinical biompedance monitor) to the server 60 can be used to calibrate the hydration measurements of the smart object 10 and improve the personalized assessment of hydration provided by the smart object 10. As an example, the determination of TBW has to account for the weight of the person and the receiving of frequent weight information from scale 65 by the electronic device 70 or server 60 can then be used to perform more accurate determinations of hydration level for the person by either providing the update weight information to smart object 10 or using the updated weight information in the TBW calculation. In addition, the hydration level for the person calculated from impedance sensors 35 can be calibrated with hydration results from the body composition scale 65 to provide a more accurate determination of the hydration level. Hydration measurements from the body composition scale 65 can be correlated with corresponding hydration measurements from the smart object 10 taken at about the same time. A relationship between the two hydration measurements can be determined and then the determined relationship can be used to adjust the hydration measurement from the smart object 10 to better reflect the actual hydration level of the user.

As described herein, smart object 10 monitors capacitive sensor 20 and one or more of sensors 14 to acquire information about a liquid, about an environment where the smart object 10 is being used, and about a user of the smart object 10. In some embodiments, the data representing this information may be processed to generate hydration and physiological data, as is described herein. In some embodiments, some or all of the data from the capacitive sensor 20, sensors 14, and user interface 12 may be transmitted elsewhere for processing, such as to electronic device 70 or server 60. Smart object 10 is in communication with the electronic device 70 via its communication interface 42, and in this manner is able to communicate with electronic device 70. In an embodiment, the electronic device 70 can determine the proximity of the smart object 10 to the electronic device 70 based on the strength of the signal received by the electronic device 70 from the smart object 10. In another embodiment, the smart object 10 may communicate directly with server 60 via network 50 without having to use electronic device 70.

Although electronic device 70 may be any suitable device for facilitating communications between the smart object 10 and server 60 (e.g., a wireless access point), in one embodiment, electronic device 70 may be a consumer electronic device such as a smartphone, smart watch (e.g., smart watch 67), tablet, laptop computer, or personal computer. Electronic device 70 has a first communication interface (e.g., Wi-Fi, Bluetooth, NFC, etc.) for communicating with smart object 10 and the smart devices. Electronic device 70 may also include one or more software programs (e.g., applications) for interacting with smart object 10, the smart devices and server 60, as well as one or more processors for executing the software of the electronic device 70. In one embodiment, a software program of electronic device 70 may include a monitoring program that includes functionality for monitoring information about the hydration of a user that can be determined based on information acquired by smart object 10 (e.g., hydration and physiological data). Electronic device 70 may also include software that provides data to perform some or all of the user interface functions for smart object 10. The display and user interface of the electronic device 70 (e.g., touch screen, microphone, keyboard, mouse, camera, etc.) may provide user interface functionality for providing information to controller 24 of smart object 10, including such information as user information or information about a liquid that is contained in smart object 10.

In one embodiment, electronic device 70 may run a hydration and liquid monitoring program. The hydration and liquid monitoring program may provide an interface for providing information regarding a liquid that is being consumed, such as by displaying visual depictions regarding the consumption of liquids, comparisons to target consumption or consumption rates, information about liquids consumed (e.g., nutritional or other information), or any other suitable information as described herein.

In one embodiment, electronic device 70 may include a camera or barcode scanner for acquiring information from a product or label. A user may also enter a search query manually, for example through voice commands, a touch screen, or a keyboard. The barcode, QR code, or manual query may be transmitted to server 60 via network 50. Server 60 may include monitoring logic 62 and database 64. The monitoring logic 62 may be implemented in software, hardware, firmware or any combination thereof. As an example, the monitoring logic 62 may include one or more processors for executing software to perform its functions, as described herein.

Monitoring logic 62 may be configured to access the database 64 based on the information received from electronic device 70 and transmit responsive information to electronic device 70 via network 50. Personal information about the user that determines personal hydration or nutrition advice can be retrieved from the server 60 or other source and used by the monitoring logic 62 to provide reminders and notifications to the user. Electronic device 70 may use this information for processing of the monitoring program and may also provide some or all of this information to smart object 10 for processing that is performed thereon. Note that the monitoring logic 62 may be implemented at locations other than the server. As an example, the monitoring logic 62 may reside on the container 11 or the electronic device 70.

The monitoring application of electronic device 70 may also display hydration and physiological data to the user. In one embodiment, hydration data that is displayed to a user by the monitoring application of electronic device 70 may include a hydration level of the user, a comparison of prior hydration levels of the user, TBW, ECW, warnings related to a low hydration level, any other suitable information, or any combination thereof.

Liquid monitoring data may be based solely on liquid consumption and the type of liquids being consumed, or in some embodiments may also be based on other health or physical information relating to a user such as hydration level. One example of liquid monitoring data that may be analyzed and displayed by a monitoring program of electronic device 70 may be monitoring data for sports and fitness applications. The monitoring program of electronic device 70 may become aware that a user is engaging in a sports or fitness activity, for example based on a user input, input from motion sensor 33 of smart object 10, inputs from motion sensors of the electronic device 70, or information provided by another device. Based on this information, and in some embodiments information related to the type of liquid being consumed, the monitoring program running on electronic device 70 may determine an optimum amount of liquid to be consumed by the user. This information may be displayed by the monitoring program and in some embodiments may also be provided to smart object 10 to provide indications to the user via user interface 12. For example, indications may provide an indication to consume more liquid, stop consuming a liquid, increase or decrease a consumption rate, change a type of liquid being consumed, and other similar information as described herein.

In one embodiment, the monitoring program may receive data from a hydration (or impedance) sensor 35 that provides a measurement indicative of the user's hydration. In this regard, the hydration sensor 35 may communicate through sensor interface 45 and be in contact with the user's skin in order to provide a hydration measurement indicative of the user's hydration level (e.g., indicating whether the user is dehydrated or overhydrated and/or an extent to which the user is hydrated). The hydration sensor 35 may communicate the hydration measurement to the electronic device 70 via the smart object 10, and the monitoring program may use the data from the hydration sensor 35 as a factor in monitoring the user's hydration. As an example, the monitoring program may determine when to indicate to the user that he or she should consume liquid based on the hydration measurement.

The monitoring program can provide for the seamless monitoring of bioimpedance and hydration of the user. The smart object 10 can provide numerous (e.g., more than 20) bioimpedance and hydration measurements per day that can be used to establish a personal measure of hydration. The monitoring program can then report relative changes of the personal level of hydration of the user. The personal measure of hydration provided by the monitoring program can provide a better assessment of relative changes and serve as an input to a notification and warning service for the user, informal care providers, or hospital or nursing home staff. All hydration measurements from smart object 10 can be automatically updated in the personal medical record for the person for use by medical professionals. The smart bottle 10 can also provide immediate feedback to the user using LED indicators for: a. Euhydration/normal hydration level (Green LED)—less than 1% decrease of the Total Body Water (TBW); b. Mild dehydration (Yellow LED)—1-2% decrease of the TBW; and c. Dehydration (Red LED)—more than 2% decrease of the TBW.

In another embodiment, the monitoring program of electronic device 70 may optimize liquid consumption for a health application. For example, users with certain kidney or heart problems may be limited in the amount and types of liquids that they can consume daily. The monitoring program of electronic device 70 may utilize information relating to the hydration level of the user, the amount of liquid being consumed, consumption rate throughout the day, and type of liquid to optimize the amount and types of liquid being consumed. In one embodiment, the monitoring program may tailor a liquid consumption regimen for a user based on known health conditions. This liquid consumption regimen may provide a user with information relating to the types of liquids that should be consumed, when they should be consumed, and at what rate they should be consumed. This information may be displayed at electronic device 70 and may be transmitted to smart object 10 to be displayed at a user interface 12.

The monitoring program can perform a dynamic assessment of the kidney function for a patient in an embodiment. Every consumption of a predefined threshold in the amount of liquids can be treated as a step function of stimulation by the monitoring program. Every time the smart object 10 and impedance sensors 35 are used, the monitoring program can determine the change of TBW and ECW as a function of new liquids and overall metabolic state (e.g., activity, ambient temperature and humidity, etc.). Continuous measurements by the smart object 10 (i.e., each time the person touches the smart object 10) may be used to assess the dynamic response of the kidneys and the overall physiological state of the person. In addition, the detection of hydration level by the smart object 10 allows the monitoring of kidney patients, not only by monitoring the amount of liquids consumed by the patients, but also by monitoring the hydration level of the patients. A similar analysis can be performed in the case of heart patients, and an assessment of TBW/ECW accumulation as a result of heart insufficiency can be performed.

Note that the liquid consumption regimen may be based on several factors. As an example, the monitoring program may have access to a table of consumption rates for users afflicted with a certain disease or medical condition. Such rates may be personalized with user age and/or weights. Information indicative of the user's age and weight as well as the user's level of physical activity and other environmental factors (e.g., ambient temperature and humidity from electronic device 70) may be input to the system or otherwise determined (e.g., retrieved from a medical server), and the monitoring program may use such information to look up or otherwise determine the desired consumption rate from the table or formula. In addition, the consumption may be adjusted to account for the hydration level of the user.

A monitoring application of electronic device 70 may also monitor nutritional data. Based on information about the amount of liquid consumed, consumption rate, and types of liquid consumed, a monitoring application of electronic device 70 may determine nutritional information such as calories, fat, carbohydrates, sugar, sodium, alcohol, caffeine, or any other suitable nutritional information. This nutritional monitoring program may be used for health monitoring programs, may provide warnings or prompts regarding consumption, and may be combined with other nutritional monitoring programs such as programs for monitoring of food consumption. Information for a nutritional monitoring application may be displayed at electronic device 70 and may also be transmitted to smart object 10 to be displayed at user interface 12.

Any of the liquid monitoring data and nutritional monitoring data that is provided by smart object 10 or electronic device 70 may be provided by electronic device 70 to remote server 60 via network 50. Network 50 may be any suitable network for communicating data between locations, such as the Internet, cellular networks, telephone networks, any other suitable network, or any combination thereof. Remote server 60 may be one or more servers having processors and memory, or in some embodiment, may have distributed processing over a plurality of servers 60 including a plurality of servers 60 at different locations. Server 60 may include monitoring logic 62 and a database 64 or other type of memory. Server 60 may receive information and data such as liquid information, liquid monitoring data, and nutritional monitoring data from electronic device 70 over time and store that data in database 64. Monitoring logic 62 may analyze the data over time to determine consumption patterns and provide analysis for systems to optimize liquid consumption patterns. In one embodiment, monitoring logic 62 may access stored data from database 64 to identify liquid consumption excesses or deficiencies. Examples of liquid excesses may include excessive consumption of liquids high in fat, sugar, alcohol, or caffeine, or improper consumption for a particular medical condition. Similarly, deficiencies may include lack of water during periods of exercise, failure to take medications, and a general failure to consume a sufficient volume of liquids. Based on this analysis, monitoring logic 62 may adjust routines, settings, warnings, and other parameters for the monitoring application of electronic device 70 while transmitting modified parameters to electronic device 70 via network 50.

Figure 5:
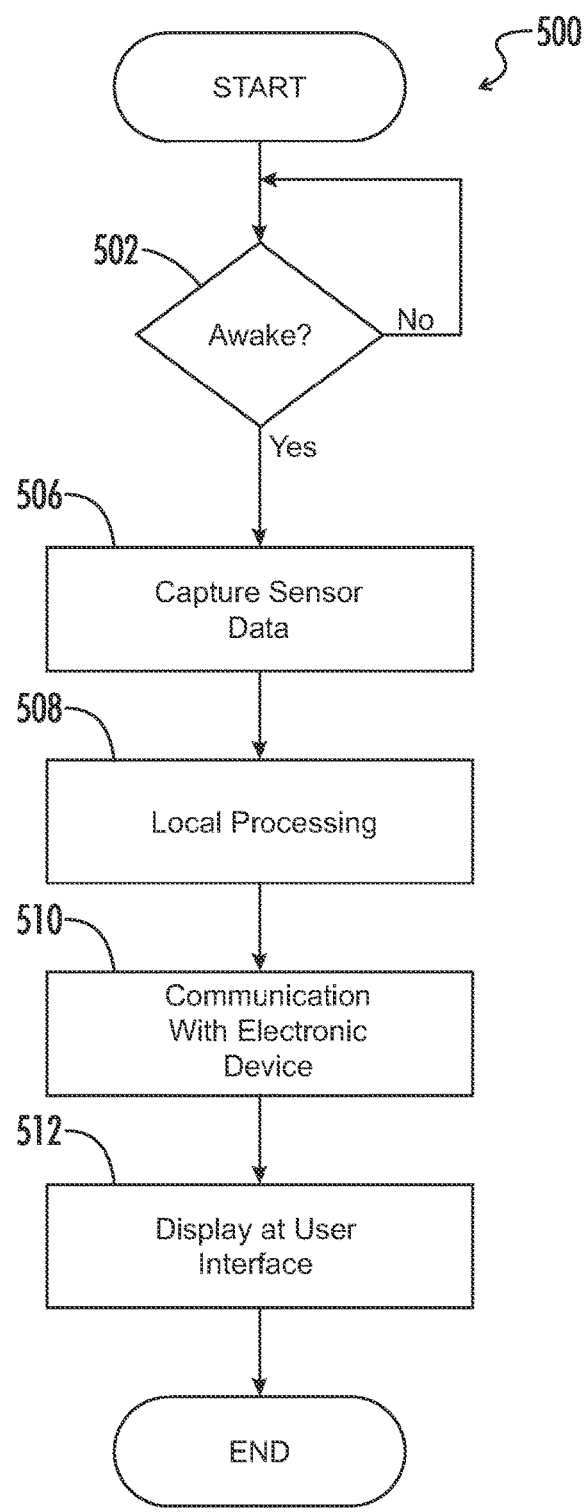
FIG. 5 shows an embodiment of a process for determining a hydration level of a person using a smart container.
Figure 6:
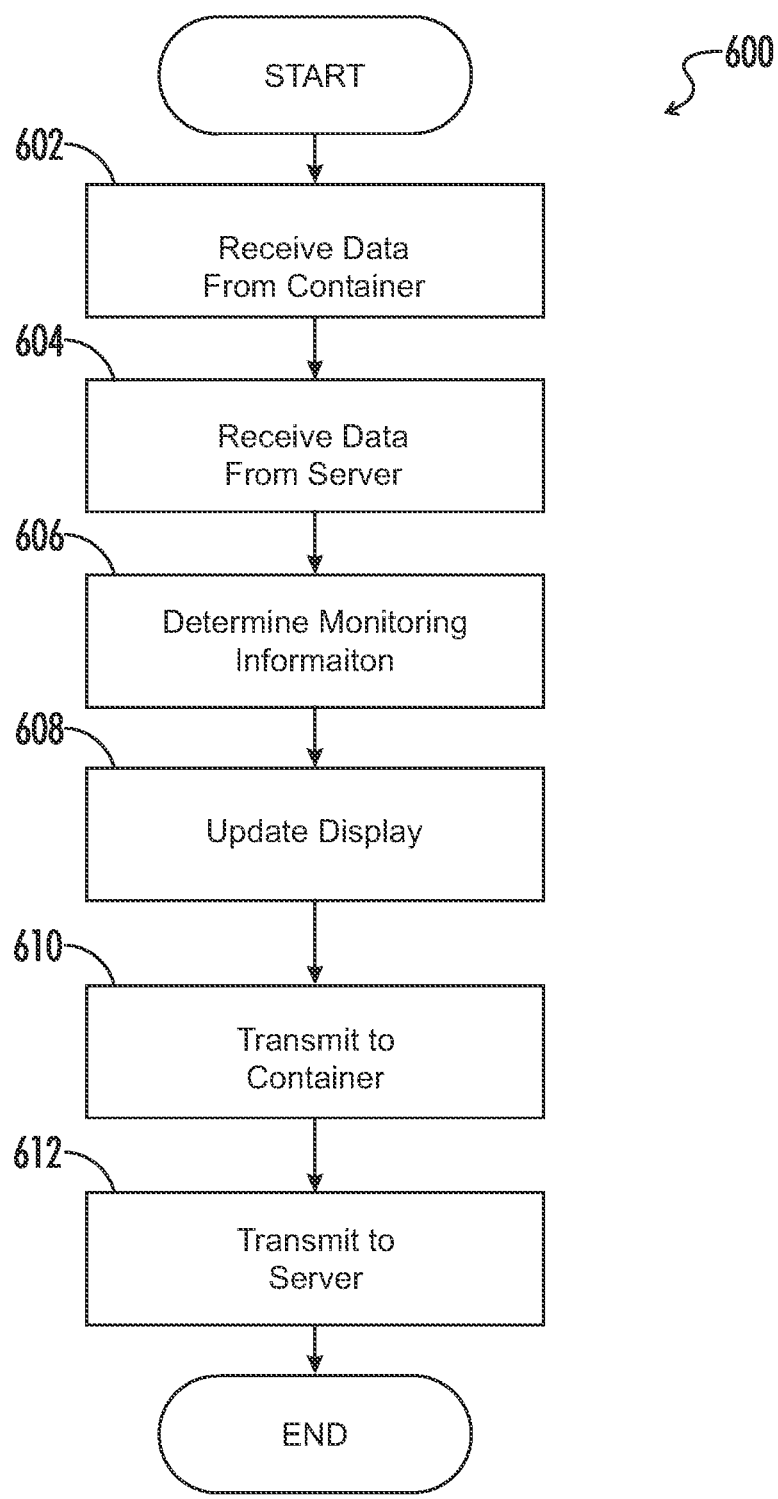
FIG. 6 shows an embodiment of a process for determining a hydration level of a person at an electronic device.
Figure 7:
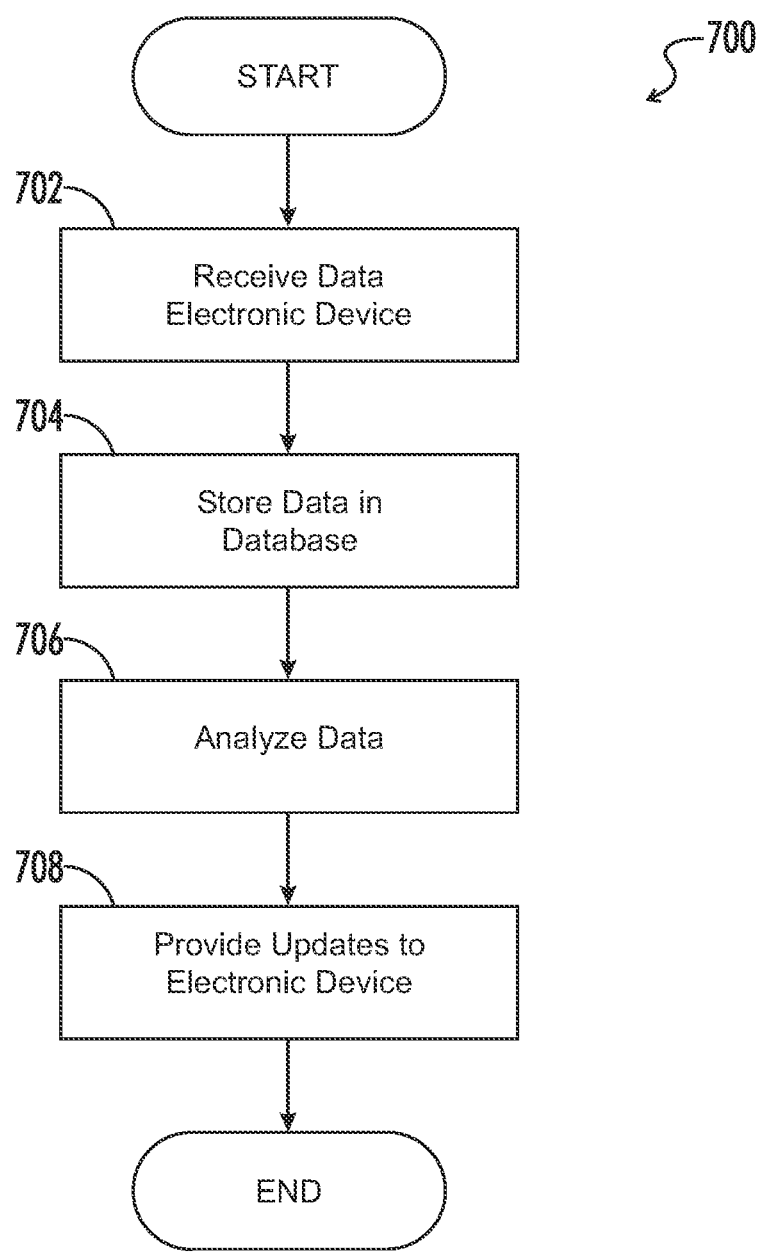
FIG. 7 shows an embodiment of a process for determining a hydration level of a person at a server.

FIGS. 5-7 show methods for determining hydration information about a person using a smart container according to some embodiments of the present disclosure. While, for purposes of simplicity of explanation, the methods are shown and described as a series of steps, it is to be understood and appreciated that such illustrations or corresponding descriptions are not limited by the order of the steps, as some steps may occur in different order and/or concurrently with other steps from what is depicted and described herein. Any non-sequential, or branched, flow illustrated via a flowchart should be understood to indicate that various other branches, flow paths, and orders of the steps, can be implemented which achieve the same or a similar result. Moreover, not all illustrated steps may be required to implement the methods described hereinafter.

FIG. 5 shows a process 500 for determining a hydration level of a person using a smart object 10. Processing may begin with smart object 10 in a sleep mode. In the sleep mode, numerous components of smart object 10 may be fully or partially disabled, thus conserving power in the sleep mode. For example, any of capacitive sensor 20, sensors 14, user interface 12, and their associated interfaces (capacitive interface 44, sensor interface 45, I/O interface 47) that are not used for waking up the smart object 10 may be disabled. Communication interface 42 may be fully or partially disabled depending on whether it is possible to receive a wake up signal from electronic device 70. Power source 43 may operate in a reduced power mode, clock 46 may provide a clock signal having a reduced clock rate, and control logic 40 may be partially shut down to provide a limited set of functionality. In one embodiment, a wake up signal may be provided by a sensor 14 such as impedance sensor 35, optical sensor 37, touch sensor 38 or motion sensor 33. Motion sensor 33 may sense movement of smart object 10, which indicates that a person may be handling the smart object. Based on this sensed activity, control logic 40 may cause the other components of smart object 10 to wake up in order to determine the hydration level of a person as described herein. In other embodiments, impedance sensor 35 (if located on the exterior of the smart object 10), touch sensor 38 or optical sensor 37 can detect touching of the smart object 10 and trigger control logic 40. In another embodiment, a wakeup signal may be provided by user interface 12 or electronic device 70 through communication interface 42. In this case, the wakeup signal may be user-initiated in order to turn on smart object 10. In one embodiment, a wakeup signal may be provided periodically based on an elapsed time determined by control logic 40 based on a clock signal from clock 46. In this manner, the components of smart object 10 may wake up periodically. Alternatively, the wake-up signal can be provided at a predefined interval in order to provide for continuous monitoring of the liquid in the smart object 10. If the smart object 10 is not awake, processing may continue at step 502 until it is awake. Once smart object 10 is awake, processing may continue to step 506.

At step 506, controller 24 may capture sensor data from impedance sensor 35 and one or more additional sensors 14. Sensor data from impedance sensor 35 may be provided to control logic 40 via sensor interface 45 and stored in memory 41. Sensor data for one or more additional sensor data 14 may be provided to control logic 40 via sensor interface 45, and then stored in memory 41. Processing may then continue to step 508.

At step 508, control logic 40 may access the user information and sensor data stored in memory or on the server and perform local processing according to one or more local processing routines. As described herein, a range of local processing routines may be available, including minimal processing such that raw user info and sensor data is provided to electronic device 70, intermediate-level processing such that data such as TBW is determined by control logic 40, and complex processing such that one or more monitoring functions are performed by control logic 40. Once the local processing has completed, the resulting data may be stored in memory 41 and processing may continue to step 510.

At step 510, control logic 40 may initiate communications with electronic device 70 via communication interface 42. Control logic 40 may transmit stored data such as liquid information data to electronic device 70. Control logic 40 may also communicate with electronic device 70 to receive information from electronic device 70, such as user information, operational parameters, user input, and updates to local processing routines to be run on control logic 40. Processing may then continue to step 512.

At step 512, control logic 40 may control the display of user interface 12 via I/O interface 47. This may include information that conveys hydration level, TBW, ECW or any other suitable data, or any combination thereof. In some embodiments, a portion of the data to be displayed at user interface 12 may have been provided via electronic device 70 or server 60.

FIG. 6 shows a process 600 for determining a hydration level of a person using the electronic device 70. Processing may start at step 602, at which electronic device 70 may receive data from smart object 10. As described herein, the received data may include raw data relating to sensor outputs, hydration or physiological data, monitoring data, or any combination thereof. A monitoring application of electronic device 70 may store the data and continue to step 604.

At step 604, electronic device 70 may receive data from server 60. Data received from server 60 may include any suitable data such as monitoring data, updates to parameters of the monitoring application of electronic device 70, or any combination thereof. The data received from server 60 may be stored in memory of electronic device 70 and processing may continue to step 606.

At step 606, a monitoring application of electronic device 70 may determine monitoring information such as hydration level as described herein. This information may be stored in memory of electronic device 70, and processing may continue to step 608.

At step 608, a monitoring application of electronic device 70 may update the display of electronic device 70. As described herein, the monitoring application may provide information to the user regarding hydration level, TBW and ECW. The user may interact with this display in response to the display data or based on additional user inputs. The display of electronic device 70 may be updated and information relating to user interaction with the display may be stored in memory. Processing may then continue to step 610.

At step 610, electronic device 70 may transmit data to smart object 10. A monitoring application of electronic device 70 may transmit data to be displayed at a user interface 12 of smart object 10, warnings or indications to be displayed at user interface 12 of smart object 10, parameter updates for performing calculations at smart object 10, software updates for smart object 10, any other suitable information, or any combination thereof. Once the data has been transmitted to smart object 10, processing may continue to step 612.

At step 612, electronic device 70 may transmit data such as hydration level, TBW, ECW, warnings, indications, any other suitable data, or any combination thereof to server 60.

FIG. 7 shows a process 700 for determining a hydration level of a person at server 60. Processing may start at step 702 at which data is received from electronic device 70 via network 50. Processing may then continue to step 704.

At step 704, server 60 may store the received data in database 64. In this manner, server 60 may accumulate a large amount of data regarding a user's hydration level and health over time. For example, physiological sensors on the container may collect physiological measures, such as heart rate, blood oxygen saturation, or galvanic skin resistance. That information can be stored on the server along with the hydration level and liquid consumption data. Once the data is stored in the database 64, processing may continue to step 706.

At step 706, monitoring logic 62 of server 60 may analyze the data that is stored in database 64. In this manner, as described herein, monitoring logic 62 of server 60 may discern long-term patterns regarding a user's hydration level or health status. Based on these long-term patterns, monitoring logic 62 may identify additional warnings or indications or may update liquid consumption routines for the user. Once monitoring logic 62 has analyzed the data stored in database 64, processing may continue to step 708.

At step 708, server 60 may communicate with electronic device 70 via server 50 in order to provide updates to electronic device 70. As described herein, those updates may include updates to monitoring protocols, warnings, indications, any other suitable updates, or any combination thereof. Once the updates have been provided to electronic device 70, processing may end.

In various embodiments described above, the hydration level of the person is estimated based on impedance measurements. In other embodiments, other types of measurements for estimating the hydration level of the person are possible. In addition, in the embodiments described herein, various functions are described as being performed at the container 11, the server 60, or the electronic device 70. It should be noted that any function performed at any of such components may be performed at any of the other components or at some other location. As an example, the monitoring of data from the impedance sensors 35 or other sensors may be performed at the container 11, the server 60, the electronic device 70, or other location.

Referring now to FIGS. 2, 3 and 4 in combination, the capacitive sensor of touch sensor 38 of FIG. 4 may also be used to measure heart rate of a user handling the smart container 10. For each cardiac cycle (i.e., heartbeat), a pressure wave (change in blood volume), or pulse, propagates through the user's vascular system. When the pressure wave propagates through blood vessels in the user's hand, the dielectric constant of skin on the user's hand changes, which affects the capacitance measurements of the touch sensor 38.

In one embodiment, the controller 24 receives capacitance measurements from the touch sensor 38 via the sensor interface 45, and control logic 40 determines the heart rate from changes in capacitance that occur each time the user's heart beats. In another embodiment, portions of the touch sensor 38 are connected to a capacitance-to-digital converter (not shown) via electrical connections, and the converter is in communication with the controller 24 via a serial communication (e.g., I2C, UART, SPI, etc.) link. Also, control logic 40 may store data indicative of the user's heart rate in memory 41, and upload data to electronic device 70 or server 60 at a later time. Still further, control logic 41 may notify the user of his/her heart rate by displaying data on the user interface 12.

Figure 8A:
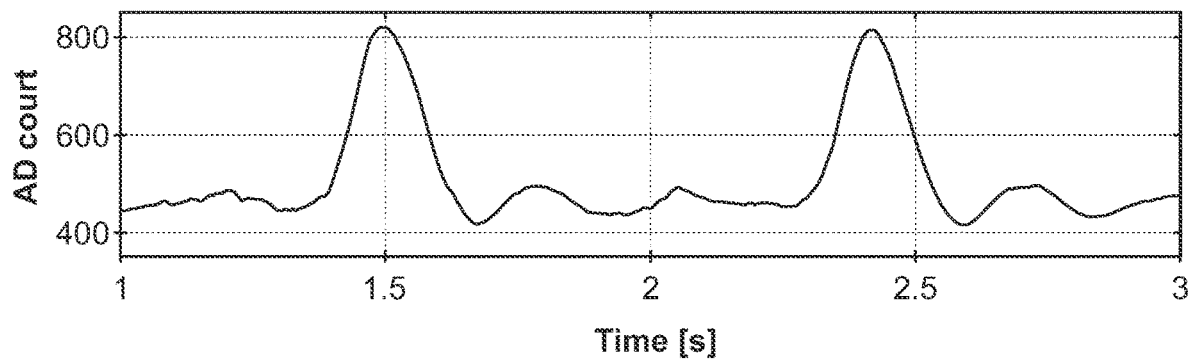
FIGS. 8A and 8B are graphical representations of a user's heartbeat detected using capacitive measurements and PPG measurements.
Figure 8B:
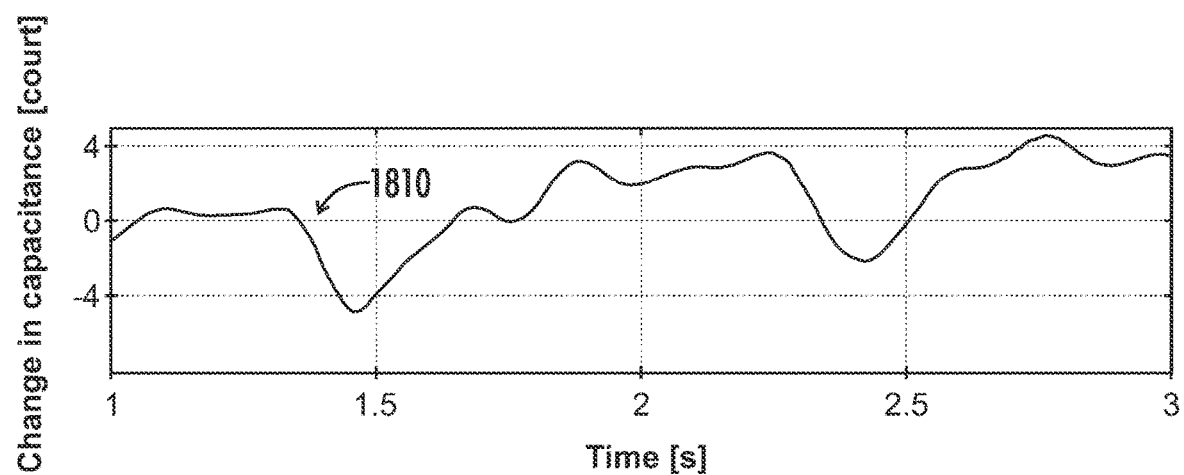

FIG. 8B depicts measured change of capacitance in time as a function of the user's heartbeat. Referring now to FIGS. 2 and 8B in combination, the graph shows a continuous-time signal 1810 that represents a sequence of two distinct heartbeats around 1.5 s and 2.4 s as seen from PPG signal in FIG. 8A. When the pressure wave, or pulse, propagates through blood vessels in the user's hand, the amplitude of the signal 1810 decreases sharply to a valley (or negative peak) value (i.e., capacitance) due to change in capacitance measurements of the body tissue for one or more of the portions of the touch sensor 38. Then, once the pressure wave subsides, the amplitude of the signal 1810 increases and returns to a steady-state value. This process occurs two times in the signal 1810, and the distance between adjacent valley (or negative peak) values represents the time lapse between heartbeats that can be used to determine heart rate. Here, the distance between adjacent valleys is 0.95 seconds, so the user's heart rate is 63.16 beats per minute.

In addition to heart rate, the change in capacitance that occurs for each heartbeat may be used by control logic 40 to assess condition of blood vessels in the user's hand. Specifically, if the blood vessels contain a substantial amount of calcium deposits, the change or pattern of change (e.g., slope of change) in capacitance may be different compared to blood vessels without calcium deposits. Further, capacitance measurements that occur after the pressure wave (that is, pulse) has left blood vessels in the user's hand may be used by control logic 40 to assess condition of capillaries and overall health of the user's vascular system.

Figure 9:
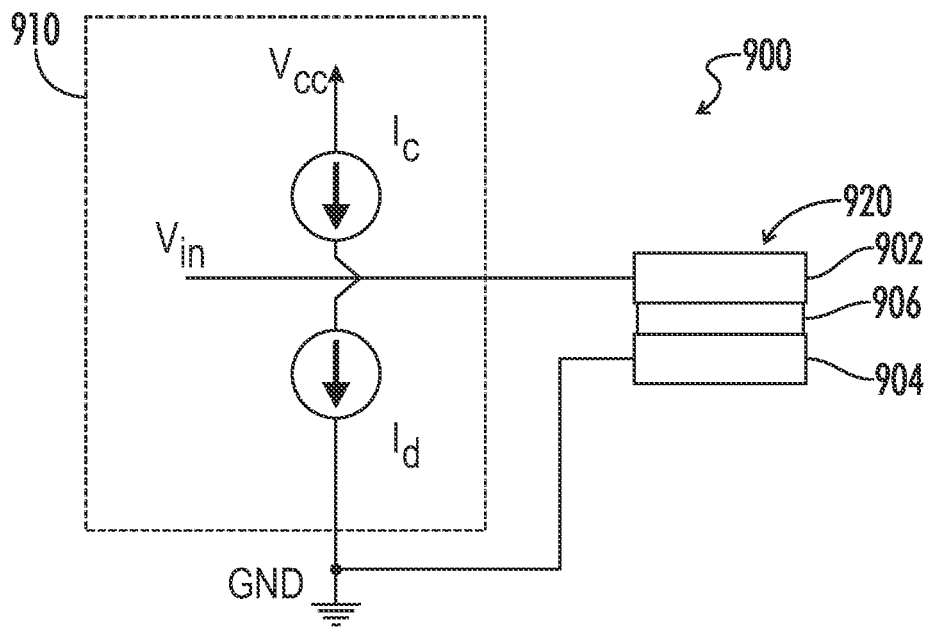
FIG. 9 shows an embodiment of a capacitance measurement system.

In other embodiments, capacitive sensors of touch sensor 38 can be used to measure other physiological parameters (e.g., blood pressure or respiration rate) in addition to heart rate. One reason for using capacitive sensors of touch sensor 38 to measure physiological parameters is that capacitance sensing consumes significantly less power than optical sensors typically used for the monitoring of vital signs. FIG. 9 shows an embodiment of a capacitance measurement system that can be used with an embedded microcontroller. The capacitance measurement system 900 can include a controller 910 connected to a sensor 920 having pair of electrodes 902, 904 with dielectric material 906 between the electrodes 902, 904. The controller 910 can convert the measured capacitance from the sensor 920 to a digital signal on one or more pins of the controller 910. In one embodiment, the controller 910 can be a Cortex-M4 microcontroller MK20DX256VLH7 that can measure capacitance on 12 pins. However, other microcontrollers with other configurations can be used in other embodiments.

Figure 10:
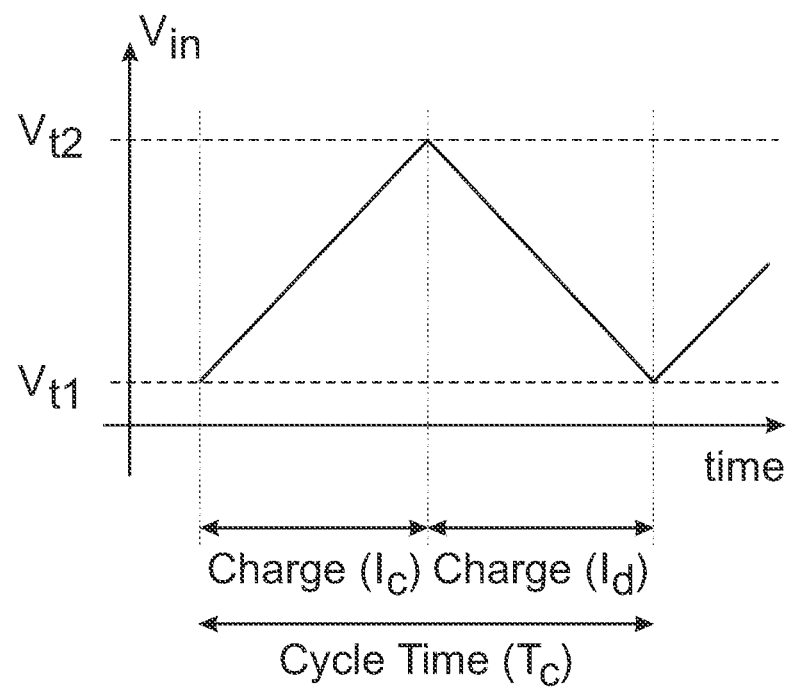
FIG. 10 is a graph of the change of voltage used during capacitance measurement with the capacitance measurement system of FIG. 9.

The controller 910 can include a sensor interface that has constant current sources, symbolically represented as $I_c$ (charging current) and $I_d$ (discharging current). In operation, the use of constant current sources causes a linear increase of the voltage on the sensor 920 (capacitor) during charging and a linear decrease of the voltage on the sensor 920 (capacitor) during discharging, as shown in FIG. 10. Voltage on the capacitive sensor 920 is monitored by the controller 910. Charging (from $V_{t1}$) by current source $I_c$ stops when the input voltage ($V_{in}$) reaches threshold $V_{t2}$. When $V_{t2}$ is reached, discharging by current source $I_d$ is activated. When the input voltage ($V_{in}$) reaches threshold $V_{t1}$, the process starts again. The total time of the charging/discharging cycle is represented as $T_c$ which can correspond to frequency based on the equation $F_c=1/T_c$.

Voltage on the sensor 920 (capacitor) at relative time t from the beginning of the cycle is shown by:

$$V_c = \frac{1}{C}\int_0^\tau I(t)dt$$

for a constant current (i.e., $I_c=I_d=I$). The voltage change during charging can be:

$$V_{t2} - V_{t1} = \frac{IT_c}{2C}$$

and $T_c$ is a function of I and C (capacitance associated with the sensor 920). In one embodiment, the capacitance cycle time and cycle frequency can be controlled by changing the charging/discharge current.

Figure 11:
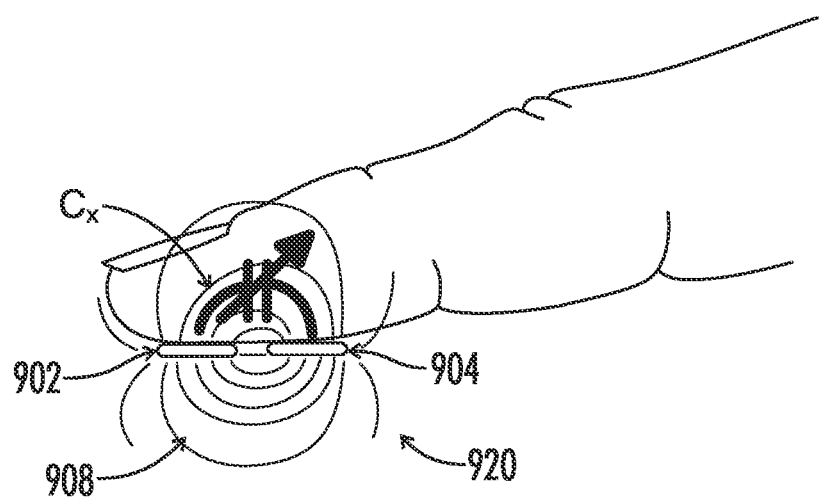
FIGS. 11-14 show different embodiments of a capacitive sensor from the capacitive measurement system of FIG. 9.

The capacitive sensor 920 can be used to detect physiological parameters of a user by sensing changes in the dielectric constant of the tissues of the user. Physiological processes (e.g., heart pumping, breathing, change of tonus of blood vessels and blood pressure, sweating, and/or a change of balance of hormones) create a change in the dielectric constant or relative permittivity ($\xi r$) in the tissues of the user. As shown in FIG. 11, two sensor electrodes 902 and 904 of capacitive sensor 920 can generate an electric field 908 that passes through the tissue (e.g., finger) of the user. Changes in relative dielectric constant of the tissue can change the capacitance between the two electrodes 902, 904. Since the measured capacitance between electrodes 902, 904 represents the sum of the capacitance of the electrodes 902, 904 without contact with the tissue and the equivalent capacitance of the tissue ($C_x$) in proximity of the electrodes 902, 904, physiological changes associated with the user can modify the total capacitance between the electrodes 902, 904 measured by the controller 910. In an embodiment, the equivalent tissue capacitance $C_x$ can be frequency dependent. The controller 910 can change the charging and/or discharging current to adjust cycle frequency $F_c$, as described above. By changing the cycle frequency, as well as the sensor configuration, the changes of capacitance caused by physiological changes (e.g., pulsatile blood flow) can be amplified for easier detection and processing.

In another embodiment, capacitive sensor 910 can be used for in-vivo analysis of body tissues as a replacement for bioelectrical impedance analysis due to the sensor's small size, galvanic isolation, and adjustable frequency. The ability to have an adjustable scanning frequency in the sensor can permit application and condition specific monitoring of tissue properties, such as detection of malignant tissues.

Figure 12:
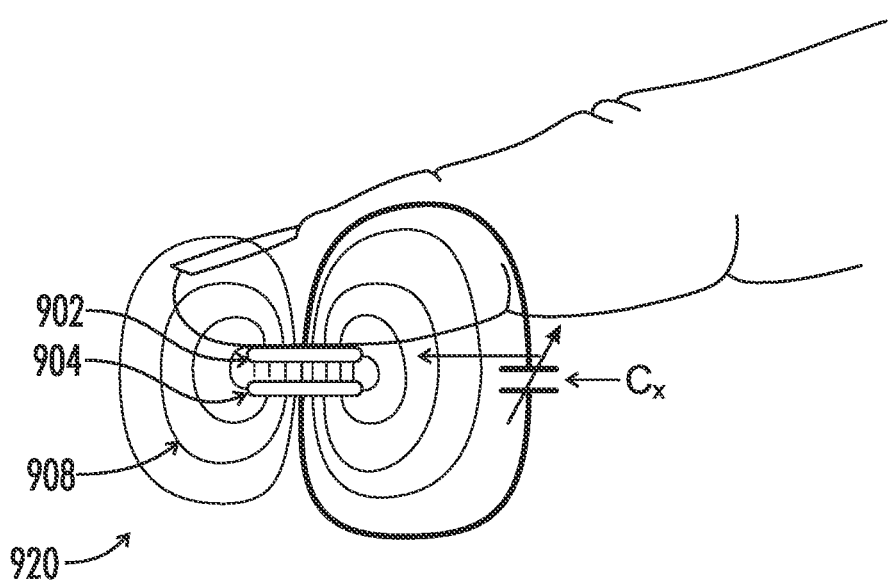
Figure 13:
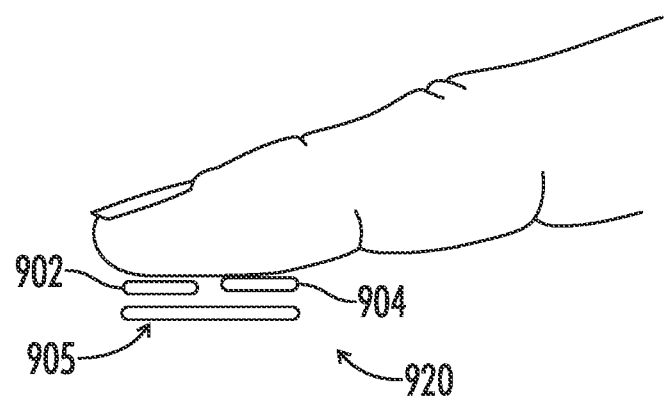
Figure 14:
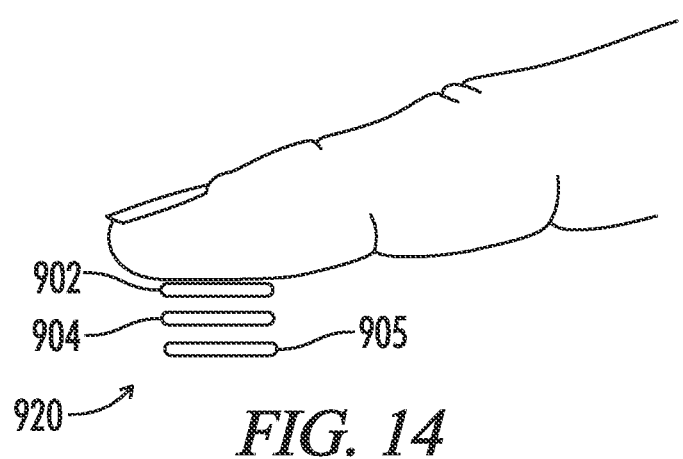

In a further embodiment as shown in FIG. 12, the electrodes 902, 904 can be positioned in a "stacked" or vertical arrangement in place of the "side-by-side" or horizontal arrangement of electrodes 902, 904 shown in FIG. 11. In another embodiment, the electrodes 902, 904 can be configured to conform to the body tissue of the user (e.g., have a curved portion to accommodate a curved portion of the body tissue. The electric field 908 shown in FIG. 12 is also influenced by the dielectric constant of the tissue of the user. The equivalent measured capacitance from sensor 920 can reflect physiological changes of the tissue of the user and be used to measure physiological parameters of the user. In further embodiments as shown in FIGS. 13 and 14, the sensors 920 shown in FIGS. 11 and 12 can be shielded with a shield 905 positioned opposite the tissue (e.g., finger) of the user (or under the electrodes 902, 904 as shown in FIGS. 13 and 14). The shield 905 can reduce noise and improve the quality of the signal provided by the sensor 905. In one embodiment, the sensor shield 905 can be implemented as a solid conductive plate of one or more conductive materials (e.g., copper), a conductive mesh of one or more conductive materials, or other shielding patterns formed from conductive materials.

Figure 15:
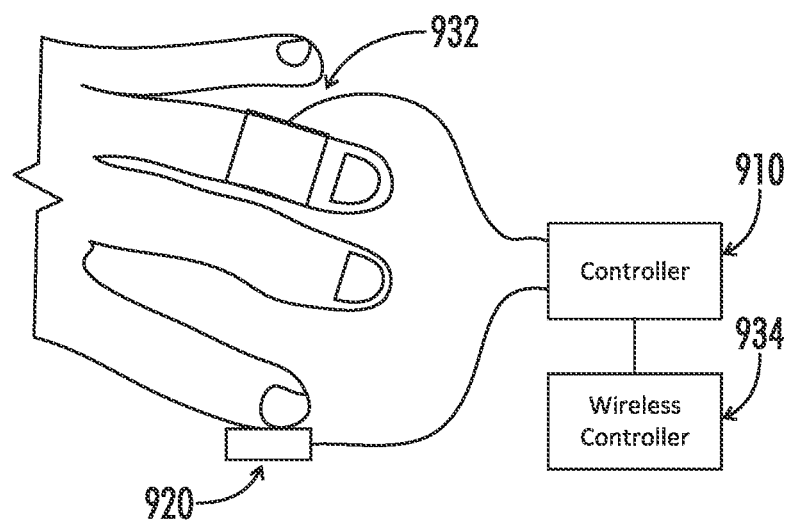
FIG. 15 shows an experimental validation arrangement for the capacitance measurement system of FIG. 9 using a PPG sensor and providing results as presented in FIGS. 8A and 8B.
Figure 16A:
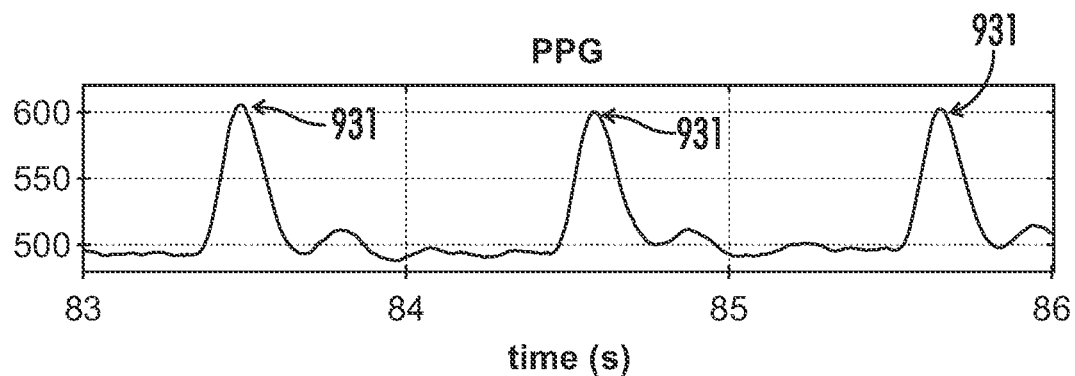
FIGS. 16A-16C are graphs of the PPG, raw capacitance and processed outputs from the capacitive sensor and the PPG sensor from the experimental arrangement of FIG. 15.
Figure 16B:
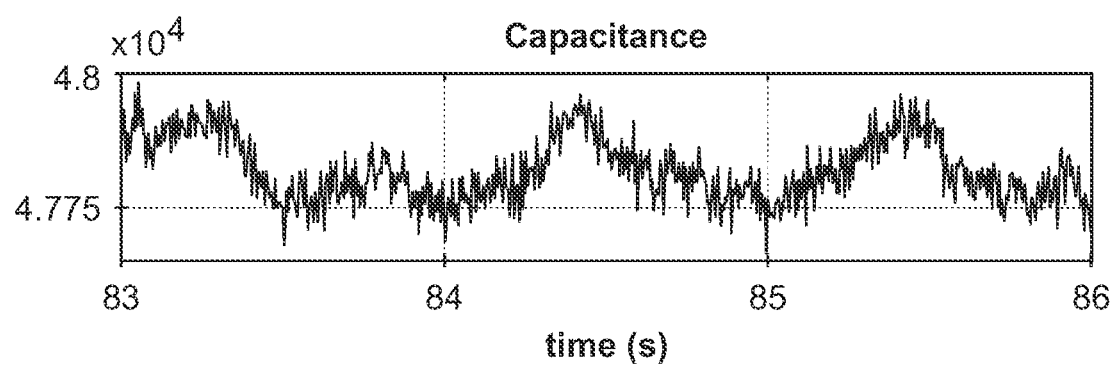
Figure 16C:
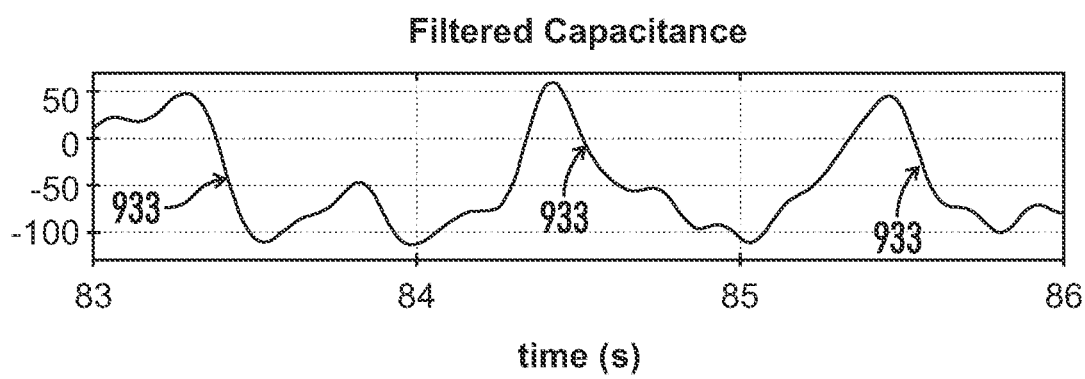

FIG. 15 shows an exemplary experimental arrangement to confirm the operation of the capacitive sensor 920 for detecting physiological parameters of a user. Reference heart activity is recorded using a photoplethysmographic sensor (PPG) 932 positioned on the ring finger. The capacitive sensor 920 is in contact with the index finger and galvanically isolated from the user. The controller 910 uses a capacitance to digital conversion to measure the capacitance from the capacitive sensor 920. The controller 910 can be coupled to a wireless controller 934 to transmit the raw (see FIG. 16B) and processed (see FIG. 16C) capacitance signals to a workstation (not shown) for archiving and visualization. FIG. 16A shows a graph of the outputs from the PPG sensor 932 and FIG. 16C shows the filtered dynamic component of the signal from capacitive sensor 920 for a period corresponding to 3 heartbeats. As seen in FIGS. 16A and 16C, for each detected heart beat (corresponding to peaks 931) from the PPG sensor 932, there is a change in capacitance (corresponding to the negative slopes and valleys 933) from the capacitive sensor 920. Therefore, based on FIG. 16C, decreases in capacitance larger than the dynamically determined threshold from the capacitive sensor 920 can correspond to heartbeats of a user and can be used to detect physiological parameters of the user without the need for a PPG sensor 932.

Figure 17:
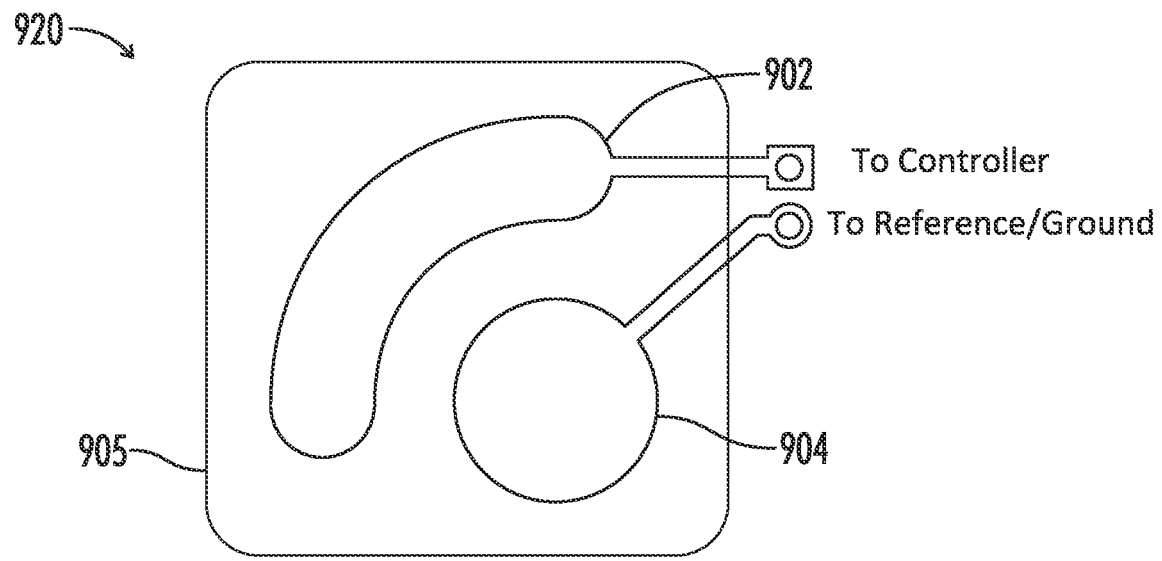
FIGS. 17 and 18 show different embodiments of the capacitive sensor of FIG. 13.
Figure 18:
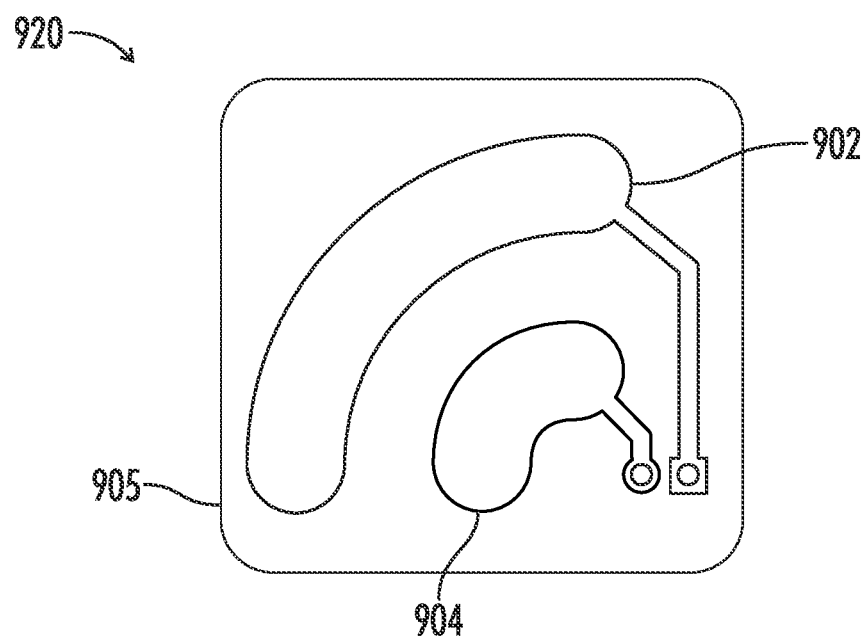

FIGS. 17 and 18 show two different embodiments of the capacitive sensor from FIG. 13. As shown in FIG. 17, the capacitive sensor 920 can include a first electrode 902 having an arcuate shape and a second electrode 904 having a circular shape. The first electrode 902 and the second electrode 904 can be positioned on shield 905 and the first electrode 902 can at least partially surround the second electrode 904. The first electrode 902 can be connected to the controller 910 to provide a signal corresponding to a capacitance measurement to the controller 910. The second electrode 904 can be connected to ground or other reference node. In one embodiment, the second electrode 904 can be connected to a ground terminal of the controller 910. The capacitive sensor 920 shown in FIG. 18 can have a similar arrangement to the arrangement shown in FIG. 17 except that the second electrode 904 can have an arcuate shape instead of a circular shape. In other embodiments, the first electrode 902 and the second electrode 904 of the capacitive sensor 920 can have any suitable shape (e.g., solid circle, ellipse, rounded rectangle, etc.) and/or can be arranged in any suitable pattern on the shield 905. In a further embodiment, the size and/or arrangement of the capacitive sensor 920 can be based on the location of the tissue of the user being used to monitor physiological parameters. For example, the monitoring of physiological parameters of a user on a finger of the user requires the capacitive sensor 920 to have a size that correspond to the tip of the finger or finger of the user. In another embodiment, a plurality of capacitive sensors, such as capacitive sensors used with touch screen technology, can be used to monitor physiological changes and a common component of capacitance from the individual sensors with the cancelation of noise from the individual sensors.

Figure 19:
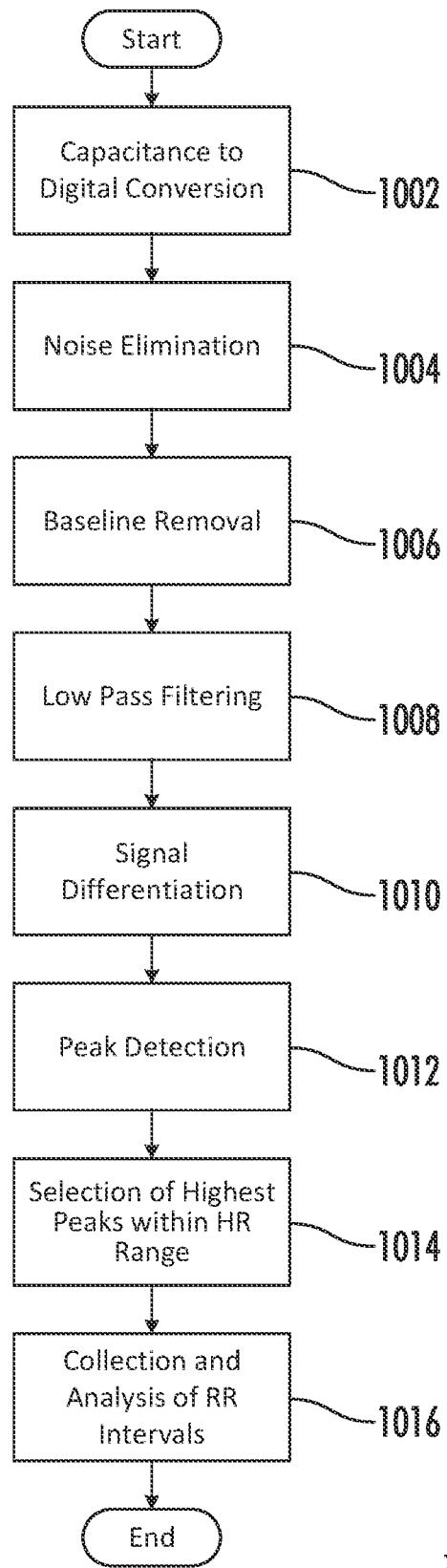
FIG. 19 is a flow diagram for an embodiment of a process for determining physiological parameters of a user with a capacitive sensor.
Figure 20A:
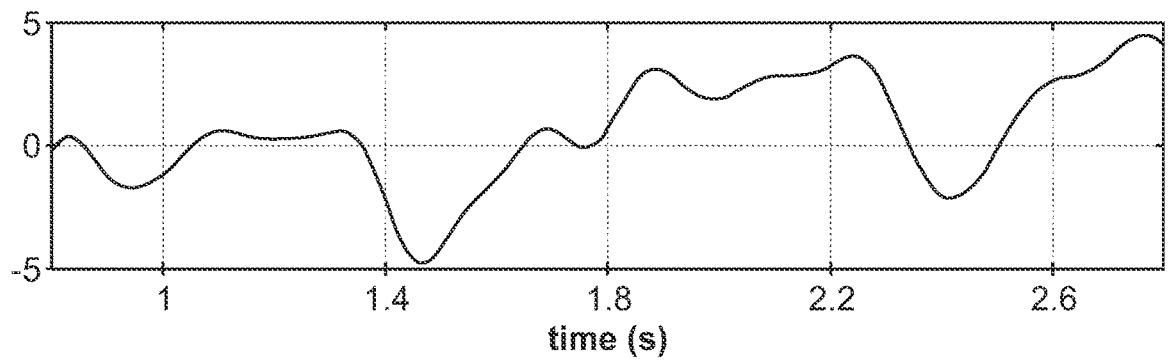
FIGS. 20A-20C are graphs of signals from different steps of the process of FIG. 19.

FIG. 19 shows an embodiment of a process for determining physiological parameters with signals from a capacitive sensor. The process begins with the measured capacitance signal from the capacitive sensor 920 being provided to the controller 910 and converted to a digital signal corresponding to a numerical value that can be processed by one or more algorithms on the controller (step 1002). Noise in the digital signal can be removed (step 1004) by using a low pass filter and/or downsampling (e.g., reducing the sampling rate) of the digital signal. The baseline of the digital signal can then be removed (step 1006) by subtracting the value of the first sample in the processing window. In other embodiments, the baseline may be removed by subtracting a mean value of all samples in the processing window, eliminating the linear trend of data in the processing window or by using other suitable baseline elimination techniques. The digital signal can then be filtered with a low pass filter (step 1008) as shown in FIG. 20A. In one embodiment, the filter can be a low pass FIR filter with a cut-off frequency in the range of the second harmonic of the maximum heart activity (approximately 5-8 Hz). In another embodiment, wavelet filtering can be used to eliminate or remove noise and/or the baseline and filter the signal.

Figure 20B:
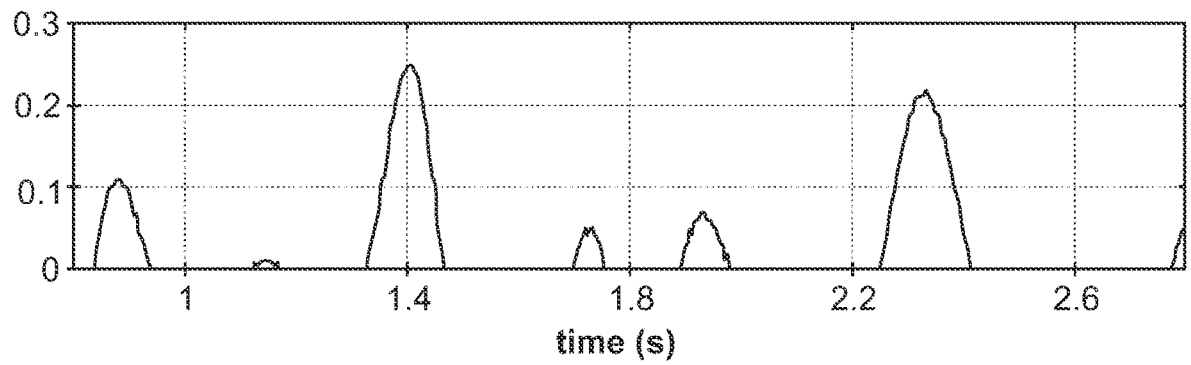
Figure 20C:
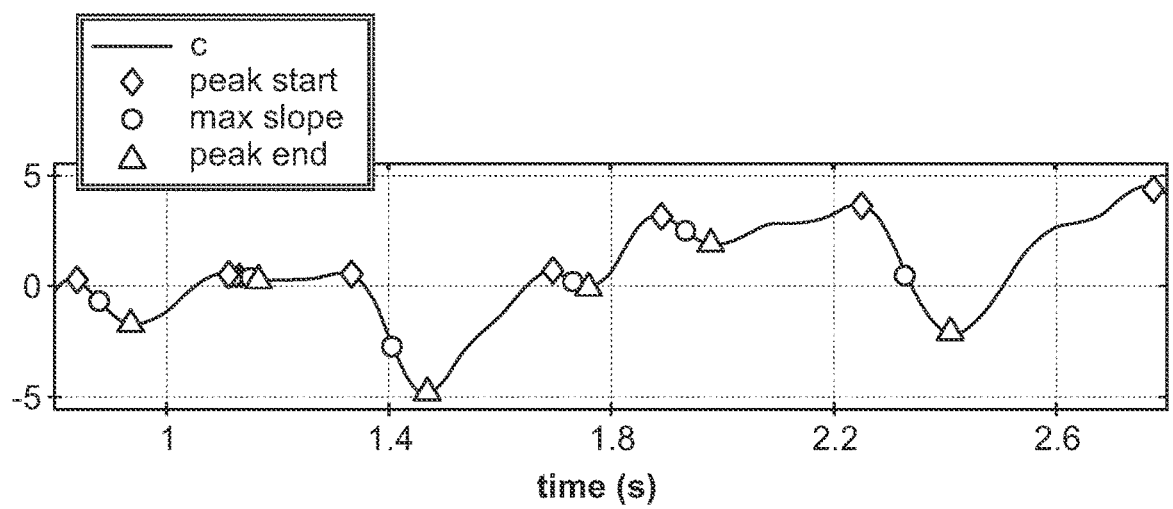

Signal differentiation is then performed on the digital signal (step 1010) to obtain a differential signal and select only negative slopes of the signal. The absolute value of the signal from signal differential and the selection of negative slopes is shown in FIG. 20B. Peaks in the differential signal are then detected (step 1012). In an embodiment, the differential signal can be searched for positive and negative peaks in the original signal as a series of positive or negative differentials in order to detect heart beats and eliminate any dependence on the baseline variation. Peak candidates are selected based on the height and width of the peaks in the original signal. Final peaks are selected according to their intensity and physiological expected range (or heart rate (HR) range) of the signals (step 1014). Peak candidates are shown in FIG. 20C with marked beginning, end, and maximum of each candidate peak. For the threshold of 0.15 of signal differentials (see FIG. 20B) only two peaks are selected in the window with maximum slope at $t_1$=1.4 s and $t_2$=2.3 s, that is correlated with corresponding peaks in a PPG signal at 1.5 and 2.4 s (see FIG. 8A). The time difference between the peaks is 2.3−1.4=0.9 s that is equivalent to 66.6 beats per minute (i.e., 60 s/0.9 s). Once the peaks have been selected, an analysis of the inter-beat (RR) interval can be performed (step 1016). With a sufficient number of RR intervals, an analysis of heart rate variability (HRV) can be performed. HRV analysis provides an assessment of the autonomous nervous system and can be correlated with the stress level of the user. In another embodiment, a Fast Fourier Transform (FFT) or wavelet spectral analysis can be used to assess average frequency of the heart activity in the processing window.

Figure 21:
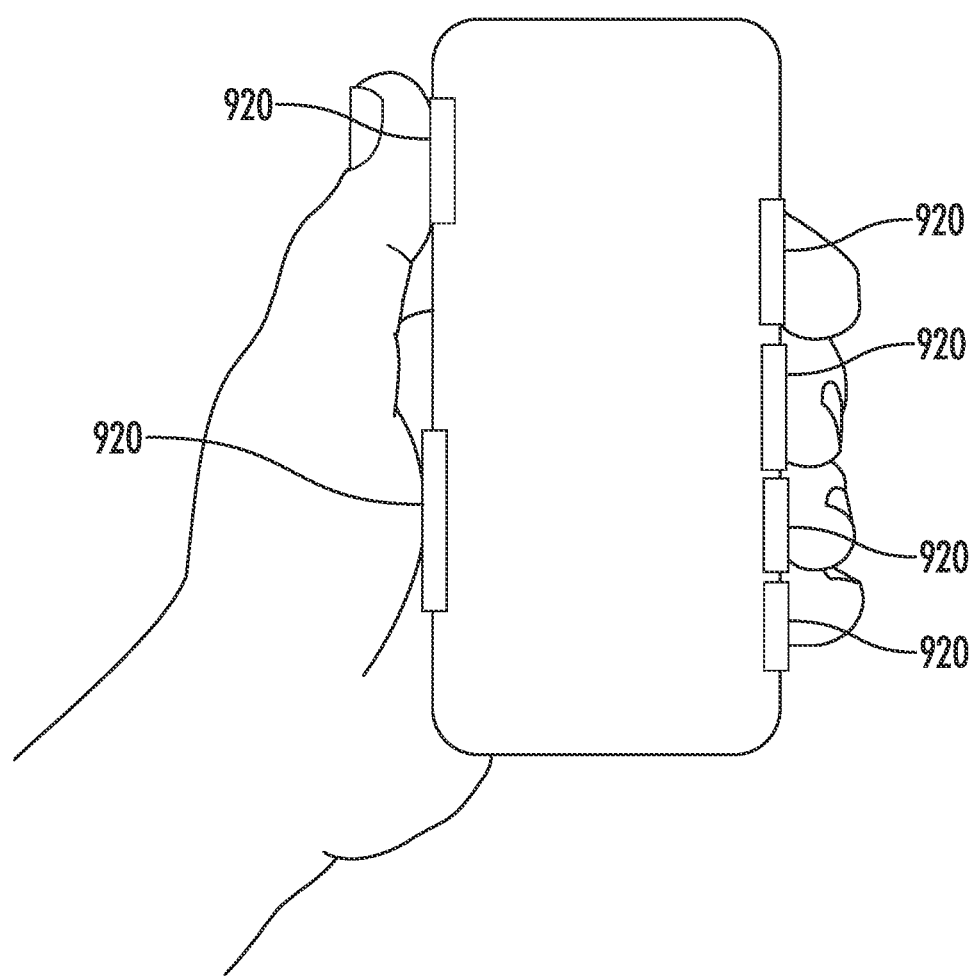
FIG. 21 shows an embodiment of a device with multiple capacitive sensors.

In one embodiment, system performance can be improved by using multiple capacitive sensors 920 (e.g., capacitive sensors 920 under multiple fingers) to achieve more robust sensing and noise elimination. FIG. 21 shows an embodiment of a smartphone or smartphone case with multiple capacitive sensors. As shown in FIG. 21, the smartphone or smartphone case can have capacitive sensors 920 positioned to be in contact with the fingers and palm of the hand of a user holding the device in order to monitor the heart activity of the user.

In another embodiment, a slow variation of the change of the capacitance signal from the capacitive sensor 920 can be used to assess the respiration of the user. Further, the detected breathing rate from a user and changes in the user's RR intervals could be used to assess the function of the autonomous nervous system of the user by using changes in heart rate variability (HRV) and respiratory sinus arrhythmia (RSA) that represents change of RR intervals caused by breathing. In addition, changes in the HRV of the user can be used to assess the stress of the user.

Figure 22A:
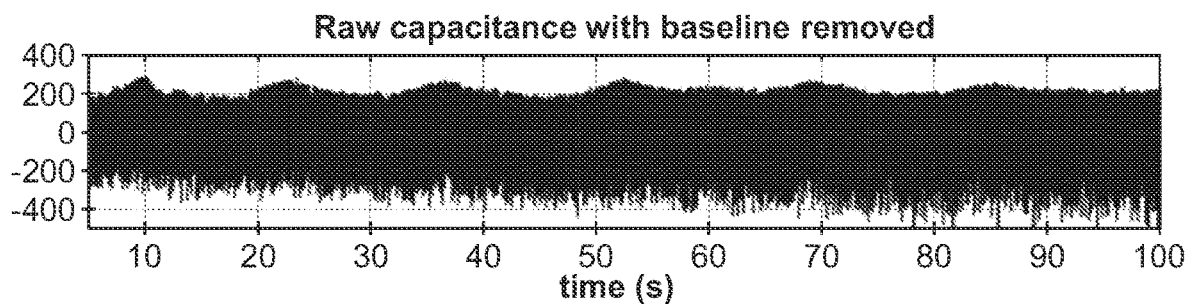
FIGS. 22A-22D are graphs of signals associated with the process of extracting a breathing signal from capacitance.
Figure 22B:
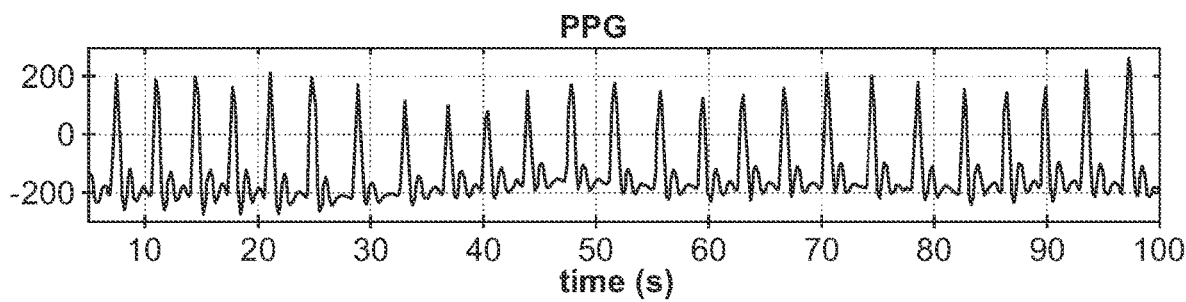
Figure 22C:
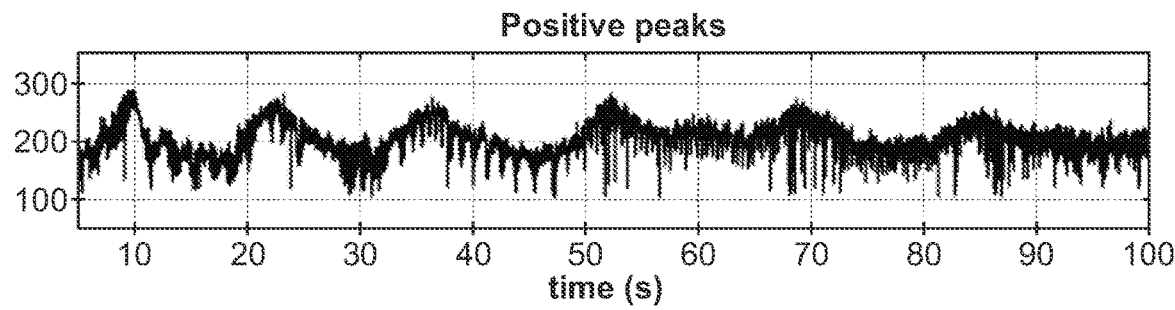
Figure 22D:
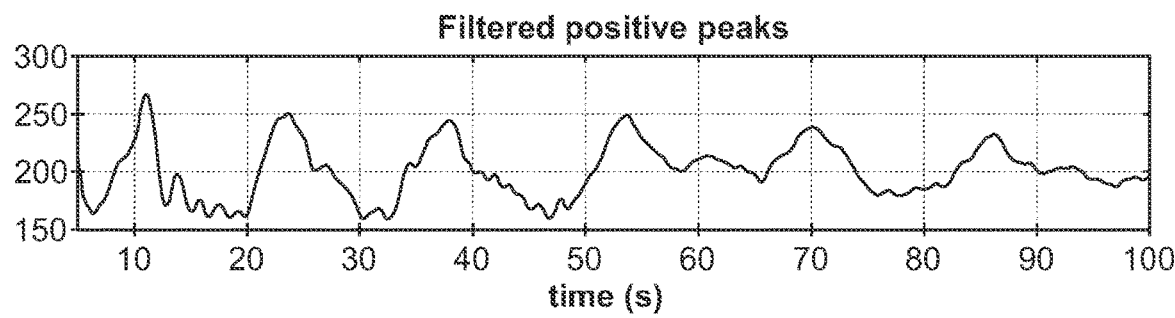
Figure 23:
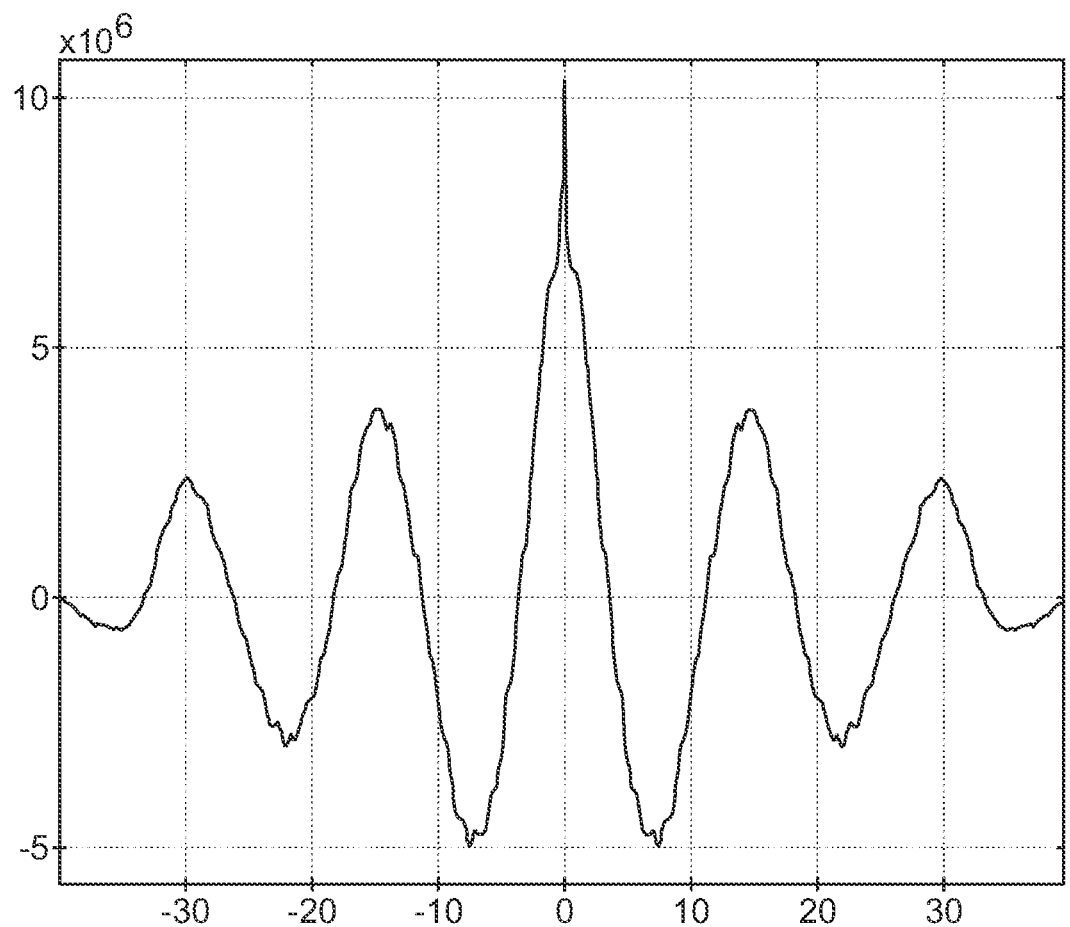
FIG. 23 is a graph of an autocorrelation of the 40 second window from the signal of FIG. 22C.

FIGS. 22A-22D represent signals associated with the process of extracting a breathing signal from capacitance measurements. Raw capacitance from the sensor with the baseline removed is shown in FIG. 22A. A corresponding PPG signal used as a reference signal is shown in FIG. 22B. The positive peaks of the raw capacitance from FIG. 22A are shown in FIG. 22C and the low pass filtered output of the signal from FIG. 22C is shown in FIG. 22D. During recording, the subject used very slow paced breathing at approximately 5 breaths per minute. Individual breaths can be identified as maximums or minimums of the filtered signal in FIG. 22D. Alternatively, breathing periods can be identified by positive or negative zero crossings of the detrended filtered signal in FIG. 22D. For example, a single breath can be identified from the maximums of the filtered signal at times 11.2 s and 23.7 s. The time difference between the maximums represents the breath duration, in this example 23.7 s−11.2 s=12.5 s, that is equivalent to 4.8 breaths per minute (i.e., 60 s/12.5 s). In another embodiment, spectral analysis or autocorrelation of the window of samples could be used to measure breathing period and determine breathing rate. FIG. 23 shows an autocorrelation of the 40 second window of the signal from FIG. 22C. Autocorrelation represents the similarity of the signal with the same signal with the time lag. Peaks of autocorrelation represent self-similarity of the delayed signal and can be used to find the fundamental frequency of the signal. For the signal in FIG. 22D, the first peak of autocorrelation is at time 14.3 s, which represents the fundamental period of the periodic signal, and in this example, the respiration period. Therefore, the average respiration rate in the given time window of 40 s was 4.2 breaths per minute (i.e., 60 s/14.3 s).

Figure 24:
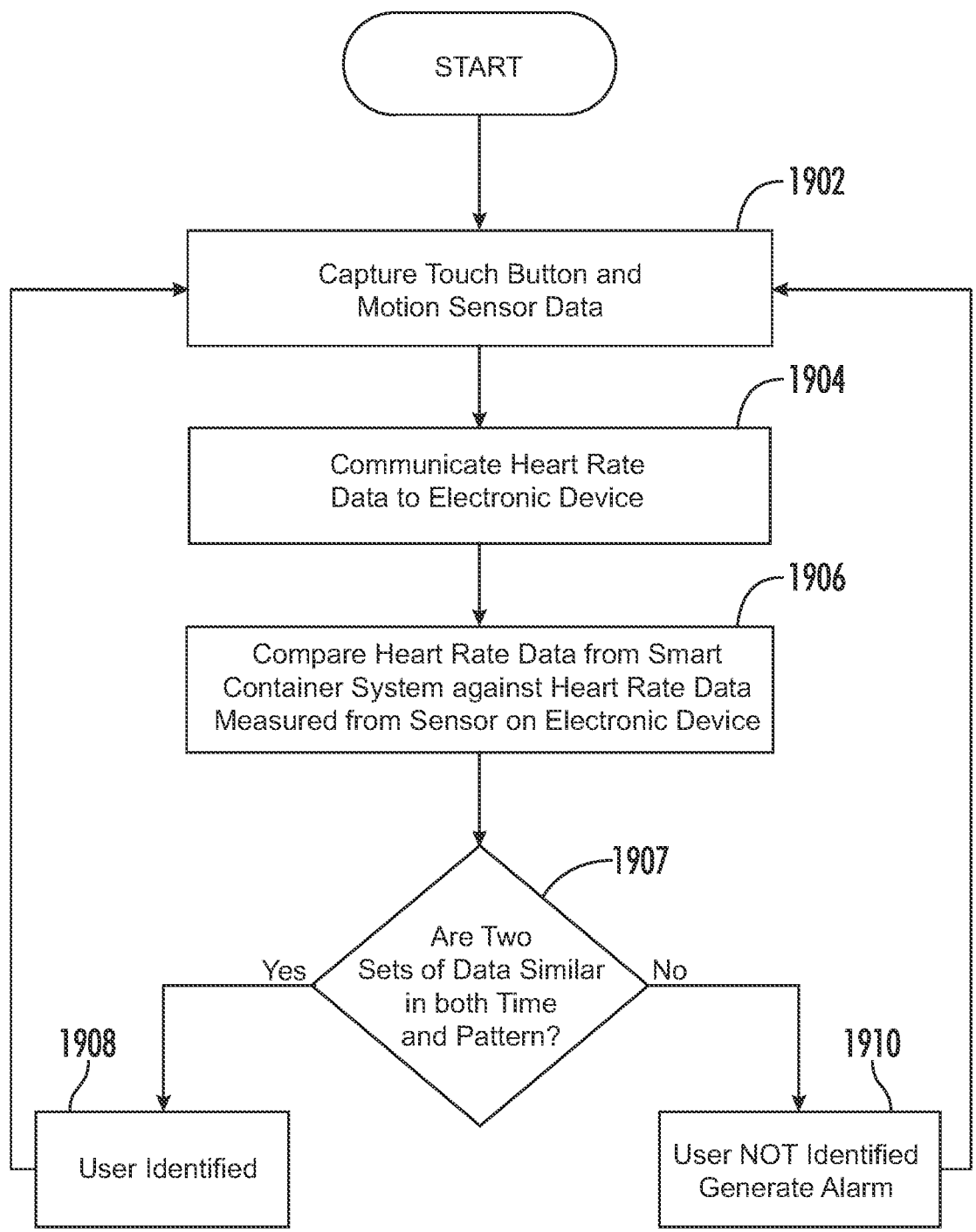
FIG. 24 shows a method for verifying identity of a user handling a smart container system based on the user's heart rate.

FIG. 24 depicts a process for identifying a user of an object (e.g., the smart container system 800) based on data indicative of the user's heart rate. Referring now to FIGS. 2, 3, 24 and 25 in combination, at step 1902, control logic 40 receives data from a capacitive sensor (e.g., capacitive sensor 920 or capacitive sensor 20) and/or motion sensor 33 indicating handling of the smart container system 800 or object 10. Next, at step 1904, control logic 40 communicates data indicative of the user's heart rate from the capacitive sensor to electronic device 70 via the communication interface 42. In other embodiments, data indicative of a user's heart rate may be provided by an optical sensor 37 in addition to or in place of the capacitive sensor.

Figure 25:
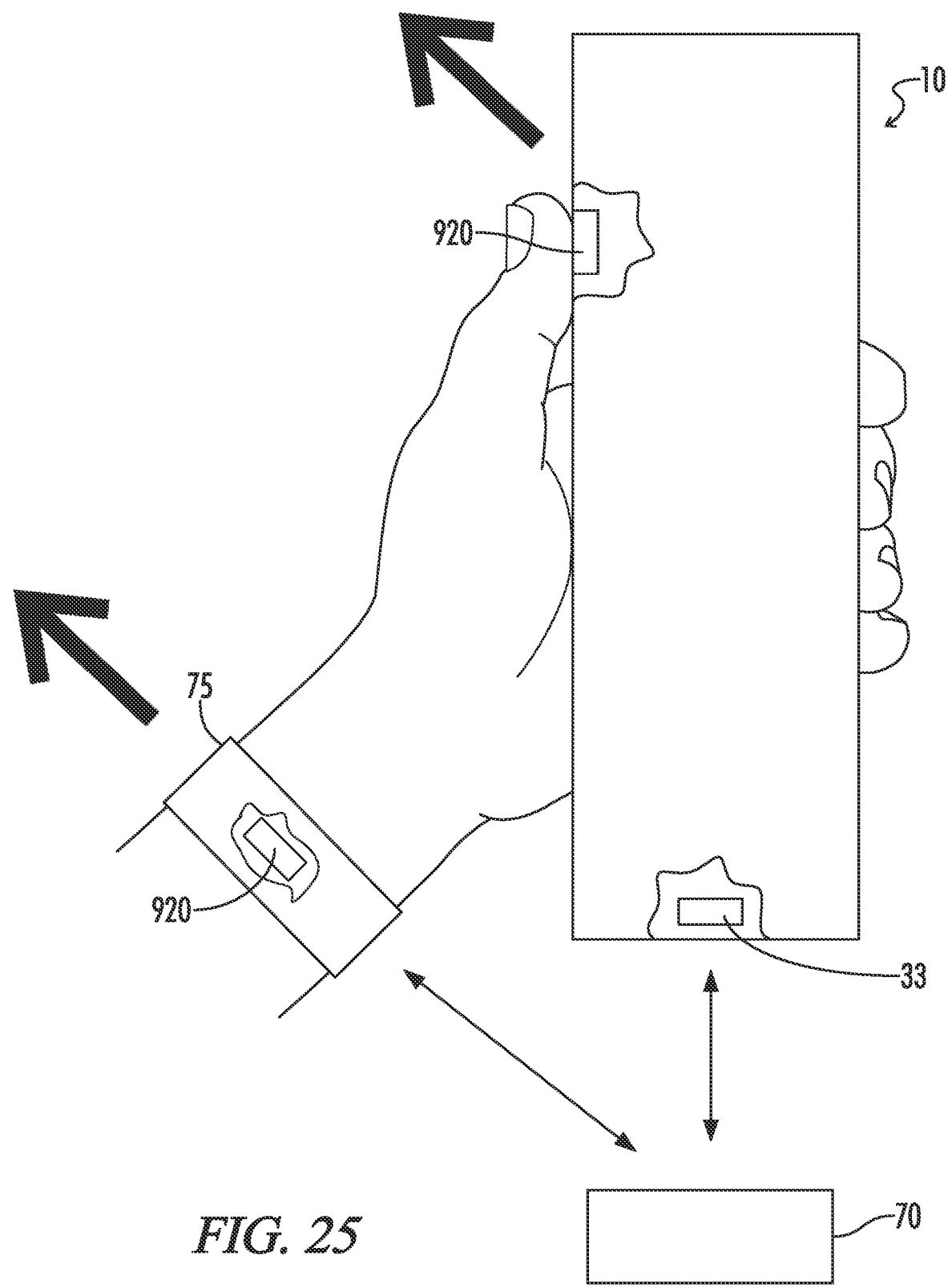
FIG. 25 shows an embodiment of an arrangement associated with the methods for identifying a user in FIGS. 24 and 26.

Then, at step 1906, electronic device 70 compares data related to heart rate (that is, capacitance measurements) from the capacitive sensor or optical sensor 37 of the smart container system 800 or object 10 against similar data collected from a pulse oximeter (not shown) or capacitive sensor (e.g., capacitive sensor 920 or capacitive sensor 20) of a wearable device 75 (see FIG. 25) on the user. In one possible embodiment, the wearable device 75 could be a smart watch with an integrated pulse oximeter and/or capacitive sensor that can communicate with the electronic device 70 either directly (as shown in FIG. 25) or through the server 60. At step 1907, if the heart rate data from the capacitive sensor of the object 10 and the heart rate data from the capacitive sensor or pulse oximeter of the wearable device 75 closely match or exactly match one another in both pattern and time, then the process proceeds to step 1908. Otherwise, the process proceeds to step 1910.

At step 1908, the electronic device 70 identifies the user by confirming that the user of the smart container system 800 or object 10 matches the person associated with the wearable device 75. Next, return to step 1902 and wait until control logic 41 receives data from the motion sensor 33 indicating motion of the smart container system 800 or object 10 or if it is requested by an external program.

At step 1910, the electronic device 70 confirms that the user of the smart container system 800 or object 10 does not match the person associated with the wearable device 75, and generates an alarm or notification on display of same and/or user interface 12 of the smart container system 800 or object 10. The same notification can be sent to the server 60 and/or the electronic device 70. Next, return to step 1902 and wait until control logic 41 receives data from the capacitive sensor and/or motion sensor 33 indicating handling or motion of the smart container system 800 or object 10. In one embodiment, the wearable device 75 and the electronic device 70 can be a single device that is worn by the user.

Figure 26:
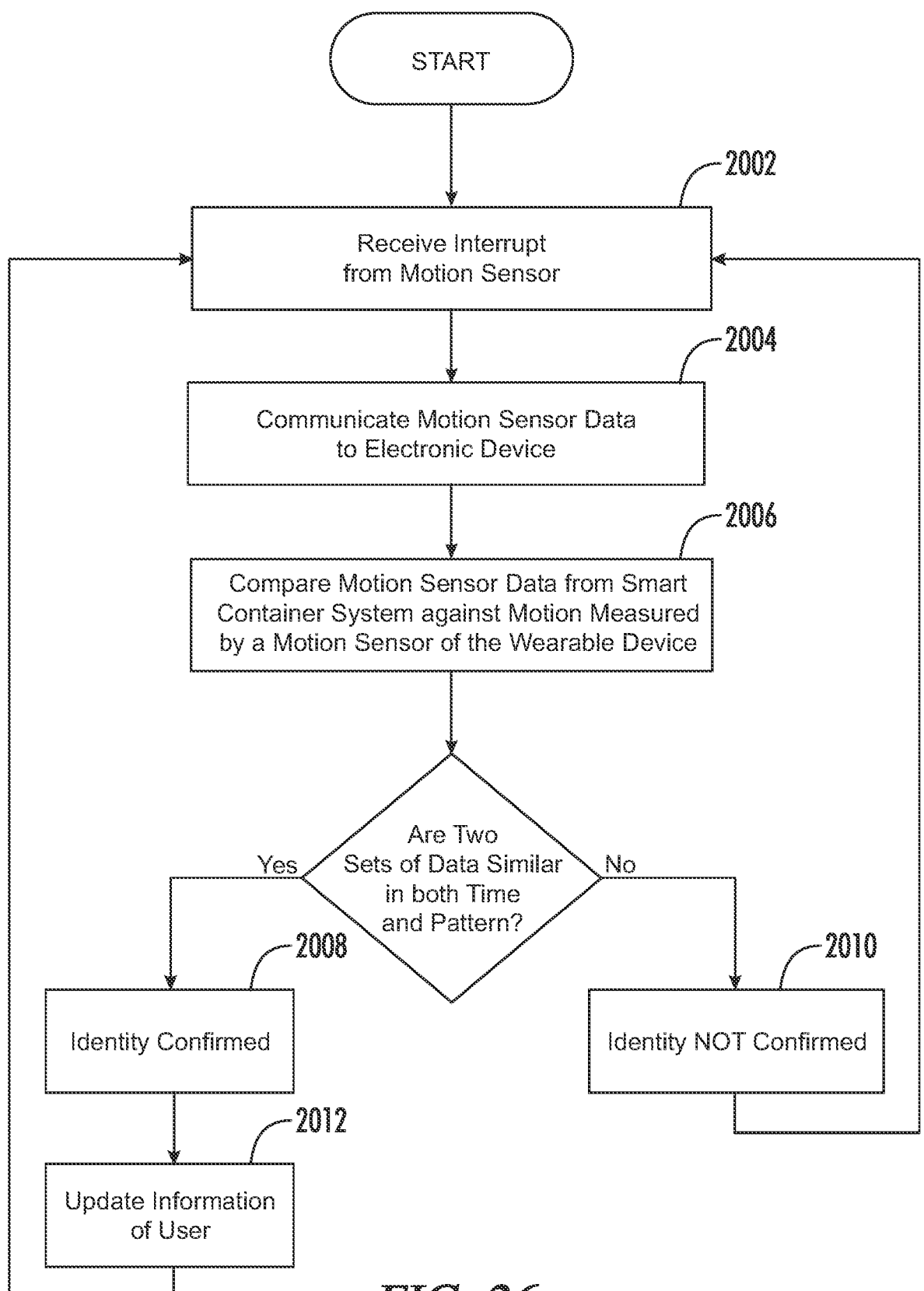
FIG. 26 shows a method for verifying identity of a user consuming liquids from a smart container based on motion sensor data.

FIG. 26 depicts steps 2000 for identifying a user of an object (e.g., the smart container system or a smartphone) based on data from motion sensor 33. Referring now to FIGS. 2, 3, 25 and 26 in combination, at step 2002, the controller 24 receives a signal from motion sensor 33 in response to a user handling the object 10 (e.g., consuming a liquid if the object 10 includes container 11). Note that, in some embodiments, the controller 24 may, prior to receiving the signal, be in a sleep or low-power mode to conserve power. Note also that it is possible for an interrupt (or other event for awakening or otherwise controlling the controller 24) to be received from other types of sensors, such as a touch sensor 38, indicating that a user is touching or otherwise manipulating the object.

At step 2004, the controller 24 transmits motion data received from motion sensor 33 to electronic device 70 via the communication interface 42. Electronic device 70 may be a smart watch or other type of device associated with the owner of the object (e.g., smart container system).

At step 2006, electronic device 70 compares motion sensor data received from the object (e.g., smart container system) against similar motion data from a motion sensor (not shown) on the wearable device 75. As shown in FIG. 25, the wearable device 75 is a separate device from the electronic device 70, but in other embodiments, the wearable device 75 and the electronic device 70 can be a single device. If the motion sensor data from the object (e.g., smart container system) and the motion sensor data from the wearable device 75 closely match or exactly match one another in both pattern (e.g., acceleration and/or orientation angle) and time, then proceed to step 2008. Otherwise proceed to step 2010.

At step 2008, the electronic device 70 confirms that the user handling the object or consuming liquid from container 11 matches the person associated with the wearable device 75. Next, proceed to step 2012, and update information (e.g., the hydration profile) of the user.

At step 2010, electronic device 70 confirms the user handling the object or consuming liquid from container 11 does not match the owner of wearable device 75. The electronic device 70 can issue a warning (e.g., an audible noise or a displayed message) to the user to notify the user that another person is handling the object or attempting to use the smart container system. In another embodiment, the electronic device 70 may instruct the object (e.g., smart container system) to issue a warning to notify the unknown user handling the object that the unknown user's handling of the object is not authorized. Next, the process returns to step 2002 and waits until the controller 24 receives another interrupt from motion sensor 33 in response to a user handling the object. In one embodiment, the electronic device 70 may transmit information about an unknown user to the server 60.

At step 2012, electronic device 70 requests, from the controller 24, data associated with the user (e.g., liquid consumption data) and updates information associated with the user (e.g., a hydration profile of the user). For example, the electronic device 70 can provide liquid consumption data to a hydration monitoring program that adjusts a user's daily target of liquid consumption based on the amount of liquid just consumed. Note that, in some embodiments, the hydration monitoring program may be located on another device, such as a smartphone. In this case, electronic device 70 communicates data directly to the other device via a wireless communication link (e.g., WiFi, 4G, LTE, Bluetooth, etc.). Alternatively, electronic device 70 may communicate liquid consumption data to server 60, and monitoring logic 62 may be used to communicate data to the other device (that is, user's smartphone). Next, return to step 2002 and wait until the controller 24 receives another interrupt from motion sensor 33 or other sensor in response to a user handling the object (e.g., consuming liquid from container).

Figure 27:
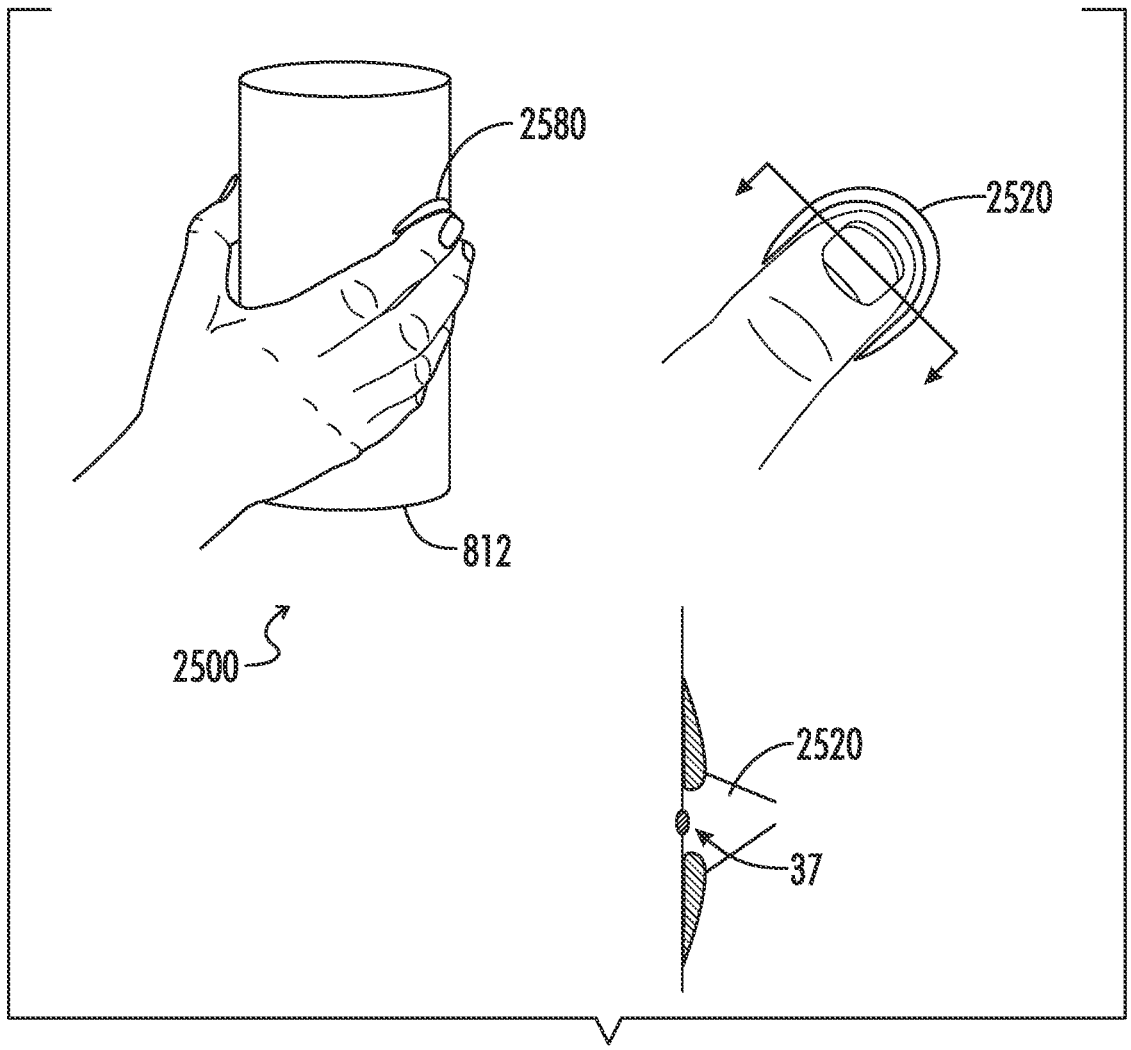
FIG. 27 shows an embodiment of a smart container having an optical sensor to detect physiological parameters of a user handling the smart container.

FIG. 27 shows an embodiment of a smart container system 2500 in which an optical sensor 37, preferably a photoplethysmography sensor, is used to measure physiological parameters (e.g., heart rate) of the user handling the smart container system 2500. Referring now to FIGS. 2, 3, and 27 in combination, the optical sensor 37 is one of sensors 14, and communicates with the controller 24 via the sensor interface 45. In one embodiment, the optical sensor 37 is located within a concave groove 2520 on the exterior surface of the outer container 812, wherein the concave groove 2520 is made sufficiently wide and sufficiently long in order to accept at least a portion of the user's finger. Thus, when a user grips the outer container 812 and inserts the distal end of a finger in the concave groove 2520, the optical sensor 37 illuminates the skin of user's finger with a light emitting diode (not shown) and then measures the amount of light either transmitted or reflected to a photodiode, also known as photoplethysmogram or PPG, (not shown). Further, based on the intensity and amount of light measured by the photodiode, the optical sensor 37 can detect changes in blood volume that occur for each heartbeat. In an embodiment, the light emitting diode can be a red, green or infrared light emitting diode.

In one embodiment, a first optical sensor 37 and a second optical sensor 37 are located within the concave groove 2520, and are separated by a predetermined length. When a user inserts her hand in the groove, both the first and second optical sensor 37 measure data based on the pulse wave that occurs during every cardiac cycle (i.e., heartbeat). Since the two sensors are separated by the predetermined length, data from either the first or second optical sensors 37 will have a time delay or latency relative to data from the other. However, dividing the predetermined length by the time delay yields the pulse wave velocity (PWV) of the blood pulse, which correlates with and can be used to estimate changes of blood pressure of the user and in some embodiments can be correlated to the hydration of the user. In addition, the interval of the PPG signal from the optical sensors 37 can be used to monitor the stress of the user.

In another exemplary embodiment, data from one or more optical sensors 37 of the smart object 10 is transmitted to an electronic device 70 and compared against similar data collected from a similar sensor on the electronic device 70 (or wearable device 75). Possible examples of an optical sensor on the electronic device 70 or the wearable device 75 could be a smartwatch that measures PPG on the wrist or an earring sensor that measures PPG on the earlobe. With a larger distance (e.g., at least 20 cm) between an optical sensor 37 on the smart object 10 that senses pulses on the tip of the finger and an optical sensor on an electronic device 70 or wearable device 75, PWV may be measured with greater accuracy. Further, if data from the optical sensor 37 of the smart object 10 closely or exactly matches data from the sensor on the electronic device 70 or the wearable device 75 in both time and pattern, then identity of the user can be confirmed based on blood pressure readings.

In another embodiment, multiple capacitive sensors (such as those in touch sensor 38) can be positioned at known distances with respect to a user can be used to measure pulse wave velocity of the blood pulse for each heartbeat of the user and assess the blood pressure (or changes in the blood pressure) for the user according to the changes in pulse wave velocity. For example, a first capacitive sensor associated with a first object held by a user (e.g., a container, smartphone, etc.) can be used to detect a first pulse wave when a finger of the user is placed in contact with the first capacitive sensor. A second capacitive sensor associated with a second object worn by a user (e.g., smartwatch, headband, etc.) can be used to detect a second pulse wave (corresponding to the first pulse wave) when the second capacitive sensor is positioned in contact with the user. The two pulse wave determinations can then be used to determine the user's pulse wave velocity, since the distance between the capacitive sensors is known (or can be determined) and the time delay between the first and second pulse waves is known. The blood pressure for the user can then be determined from the pulse wave velocity calculation and the measurements from the first and second capacitive sensors.

Figure 28:
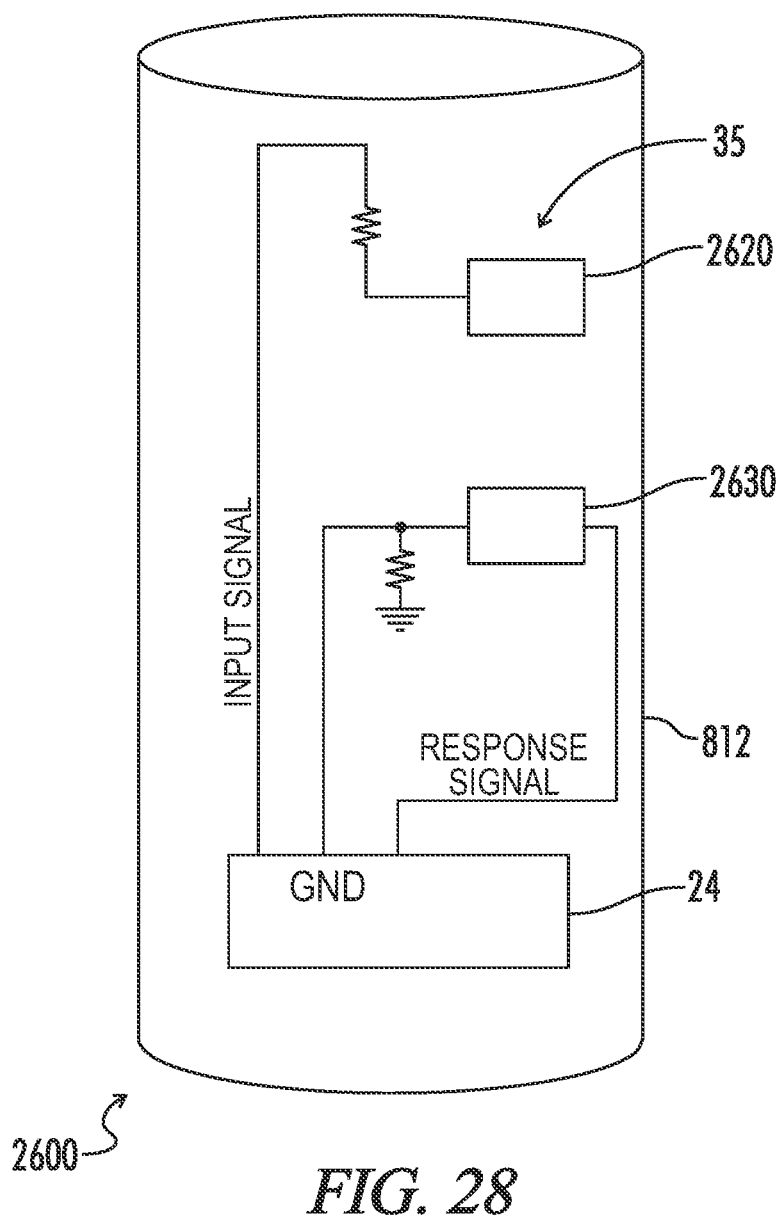
FIG. 28 shows an embodiment of a circuit that non-invasively measures emotional response of a user handling the smart container based on measurements of complex impedance from body tissue in contact with the smart container system.

FIG. 28 shows an embodiment of a smart container system 2600 in which a first set of electrodes 2620 and a second set of electrodes 2630 are used to monitor the complex impedance of the skin of the user handling the smart container system 2600. More specifically, FIG. 28 shows one implementation of a circuit that indirectly measures emotional response of a user via changes in the galvanic skin resistance of the user's hand. Referring now to FIGS. 2 and 28 in combination, in one embodiment, a constant voltage or a sinusoidal input signal at a certain frequency is generated by the controller 24 and propagates from the first set of electrodes 2620 into the skin of user's hand. The second set of electrodes 2630 measures a response signal that is, at least in part, caused by the sinusoidal input, and communicates the response signal to the controller 24. The response signal represents a voltage divider between resistors R1 and R2 and resistance of the user's hand between electrodes 2620 and 2630. Control logic 40 determines, based on the magnitude of the response signal, a value indicative of the user's complex skin impedance for a given point in time. Changes of skin impedance may be used to monitor a user's emotional response, similar to monitoring of galvanic skin resistance or GSR. Monitoring of complex impedance at several frequencies can be used to monitor changes in hydration of the user.

As discussed above, impedance sensors 35 placed on the exterior surface of the smart object 10 can be used to determine the hydration level of the person holding the smart object 10. In addition, the impedance sensors 35 used to detect hydration can also be used to detect an electrocardiogram (ECG) and the heart rate for the person. For example, a bioamplifier connected to electrodes 1302 and 1310C (see FIG. 32) would produce a clean ECG that can be used for heart rate and heart rate variability analysis. A combination of ECG and PPG can be also used to detect Pulse Wave Velocity (PWV), which is the latency (i.e., the Pulse Travel Time (PTT)) between the detected heart beat in the ECG and arrival of the blood pulse to the finger detected using the optic sensor 38. PWV and/or PTT can be correlated with blood pressure and can be used to assess blood pressure and provide an alternative correlation to dehydration, as well as stress-related physiological changes.

Figure 29:
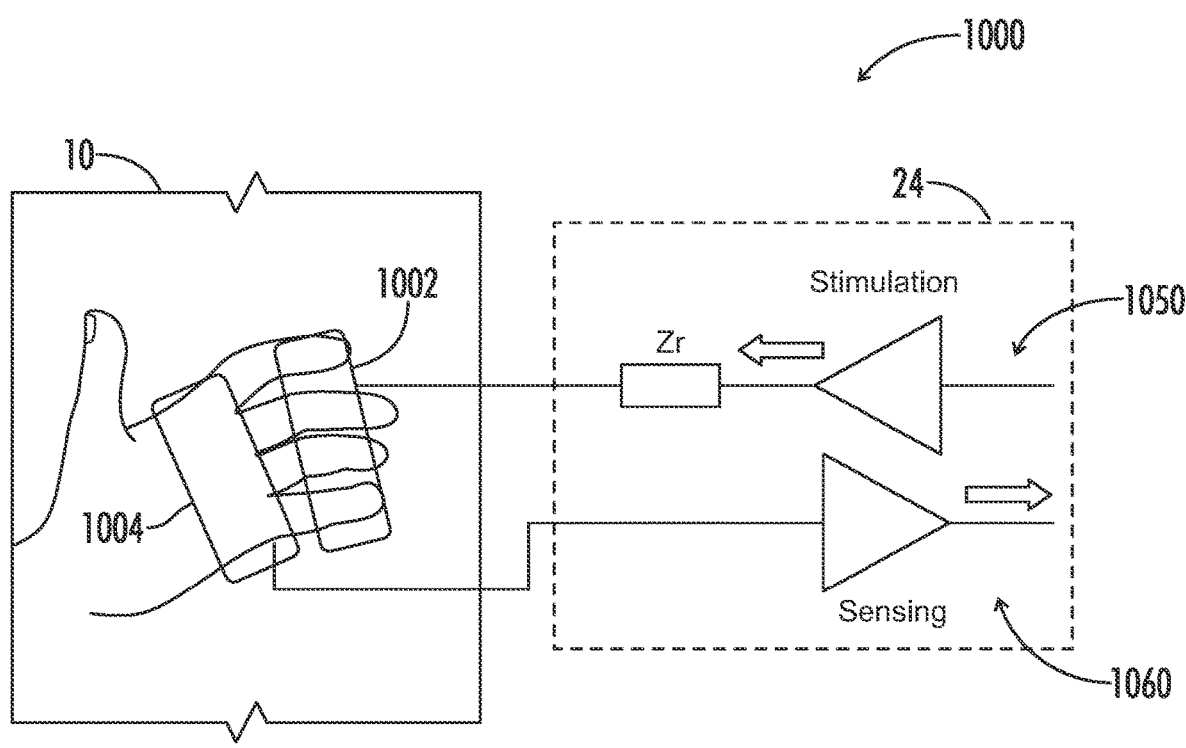
FIGS. 29-32 show different embodiments of hydration monitoring systems associated with the smart container.

FIG. 29 shows an embodiment of a bioimpedance based hydration sensing system 1000 that uses two electrodes 1002 and 1004 (i.e., impedance sensors 35) located on the exterior surface of the smart object 10. When the person grabs the smart object 10, one hand of the person can come into contact with both electrodes 1002 and 1004 as shown in FIG. 29.

The use of bioimpedance measurements to determine TBW and ECW and sense hydration level can require precise positioning of electrodes 1002 and 1004, such that repeated contact with the electrodes 1002 and 1004 occurs each time the person handles or uses the smart object 10. In an embodiment, the use of a finger guide on the smart object 10 (see e.g., FIG. 27) can be used as a reference point to determine the proper positioning of electrodes 1002 and 1004 on the smart object 10, which coincides to the area where the palm and fingers of the person come into contact with the smart object 10 when the finger guide is used.

In the hydration sensing system 1000, the bioimpedance of the person is measured using only one hand of the person. Electrode 1002 is positioned in an area corresponding to where the fingers of the person would be placed and is connected to a stimulation circuit 1050 of the controller 24. The electrode 1004 is positioned in an area corresponding to where the palm of the person would be placed and is connected to a sensing circuit 1060 of the controller 24. The complex bioimpedance of the hand is represented by Z and is dependent on the hydration level of the person. The output of the stimulation circuit 1050 of the controller 24 can be given as a voltage divider between hand impedance (Z) and a reference impedance $Z_r$:

$$V_{out} = V_{in} \frac{Z_r}{Z_r + Z}$$

Since the complex impedance Z depends on tissue hydration, the output of the circuit can also depend on user hydration. Reference impedance $Z_r$ can be selected to maximize the measured value. For example, it could be resistor with resistance equal to absolute value of expected body impedance (i.e., |Z|). In addition, since the individual contact area between the palm of the hand and the smart bottle 10 depends on the palm size and the holding pattern of the person, the electrode positioning on the smart object 10 should accommodate for these individual differences. In an embodiment, one or both of electrodes 1002 and 1004 may have a size and/or shape that can accommodate a multitude of different hand sizes. In another embodiment, if a finger guide is used on the smart bottle 10, the placement of electrode 1002 can coincide with the location of the finger guide.

Figure 30:
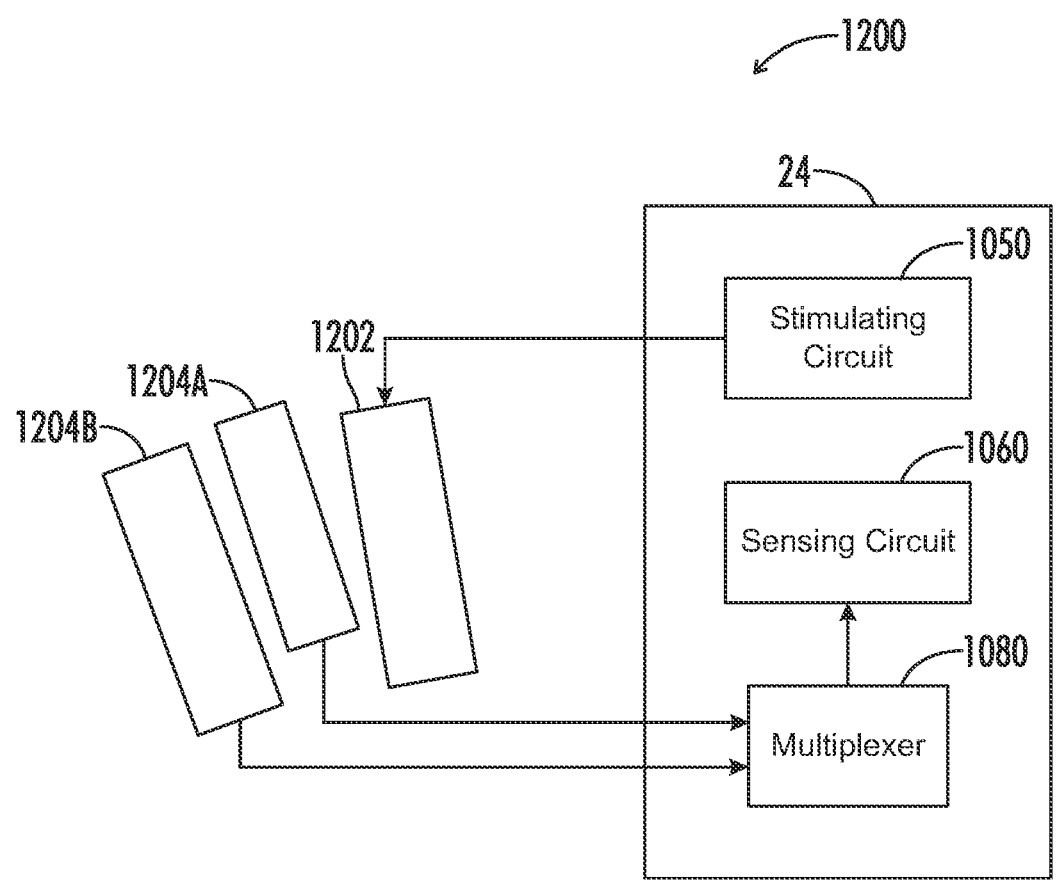

In the embodiment of the hydration sensing circuit 1200 shown in FIG. 30, several sensing electrodes 1204A and 1204B on the smart object 10 can be used with a stimulation electrode 1202 on the smart object 10 to accommodate for different palm sizes of the user. The stimulation electrode 1202 can be placed in proximity to a finger guide located on the smart object 10 and is connected stimulating circuit 1050. The proximity of electrode 1202 to the finger guide can result in good contact of the fingers, independent of the individual users. The use of two sensing electrodes 1204A and 1204B on the smart object 10 can permit a majority of people to make good contact with the palm of the hand by contacting at least one of the electrodes 1204A and 1204B. In order to determine the impedance of the person (and then the hydration level of the person), the output of only one of the electrodes 1204A and 1204B can be used. To distinguish between the outputs of the electrodes 1204A and 1204B, the electrodes 1204A and 1204B can be connected to an analog multiplexer 1080. The multiplexer 1080 can then select the signal from the select from electrode 1204A and 1204B that results in the lower absolute value of the impedance—|Z| with the stimulating electrode 1202.

While the single channel measurement by hydration monitoring systems 1000 and 1200 in FIGS. 29 and 30 can provide a hydration level for a person, the determined hydration level only corresponds to the water content only on the palm of one hand of the person. A better assessment of the hydration level of the whole body can be obtained by measuring the complex impedance across the upper trunk of the person or between the palms of the two hands. In an embodiment, a "whole body" bioimpedance measurements can use 4 electrodes–2 outer electrodes for stimulation (e.g., electrodes positioned near the fingers), and 2 inner electrodes for the measurement (e.g., electrodes positioned near the palms).

Figure 31:
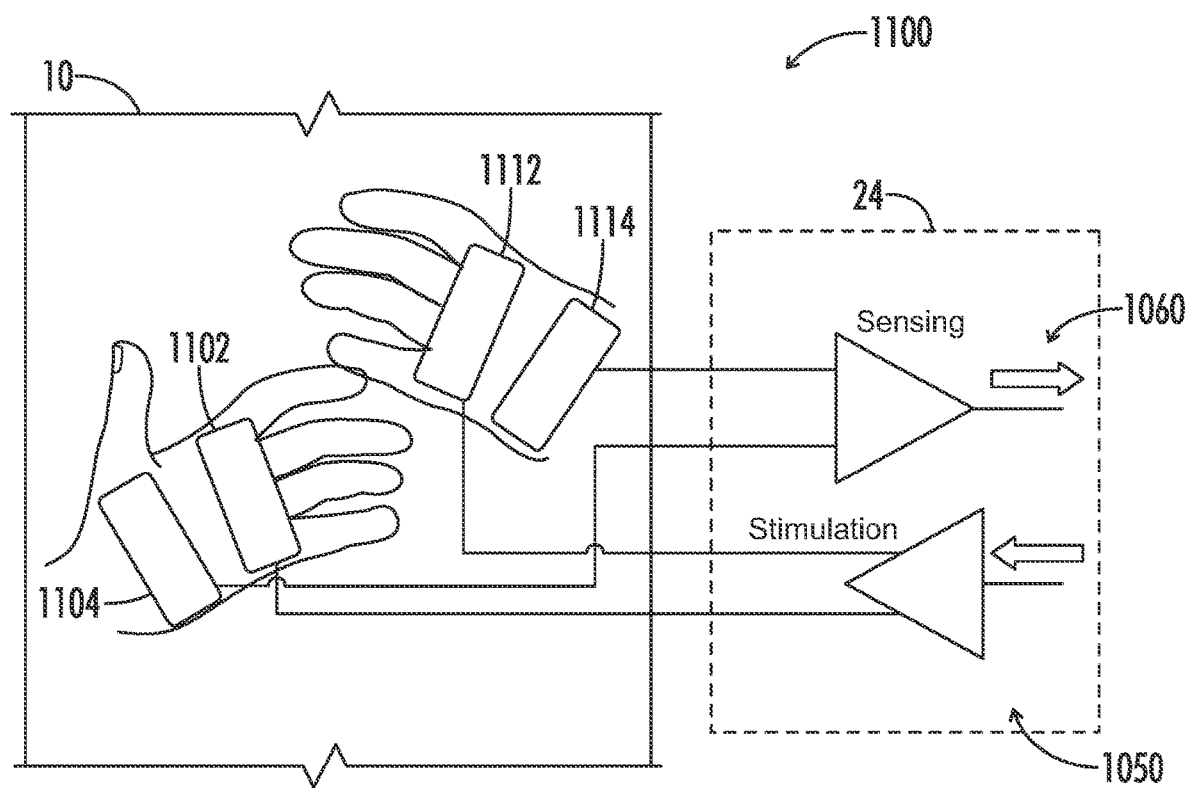

A hydration monitoring system 1100 for measuring the complex impedance of the person across the upper trunk is shown FIG. 31. Electrode 1102 is positioned on the smart object 10 in an area corresponding to where the fingers of one hand of the person would be placed and is connected to a stimulation circuit 1050 of the controller 24. The electrode 1104 is positioned on the smart object 10 in an area corresponding to where the palm of the one hand of the person would be placed and is connected to a sensing circuit 1060 of the controller 24. In order to complete the circuit across the upper trunk of the person, the smart object 10 can include a second set of electrodes for the other hand of the user. Electrode 1112 is positioned in an area corresponding to where the fingers of the other hand of the person would be placed and is connected to the stimulation circuit 1050. The electrode 1114 is positioned in an area corresponding to where the palm of the other hand of the person would be placed and is connected to the sensing circuit 1060. The stimulation circuit 1050 can provide stimulation at a given frequency to electrodes 1102 and 1112, while the signal recorded at electrodes 1104 and 1114 is recorded and processed by sensing circuit 1060 to determine the hydration level.

Figure 33:
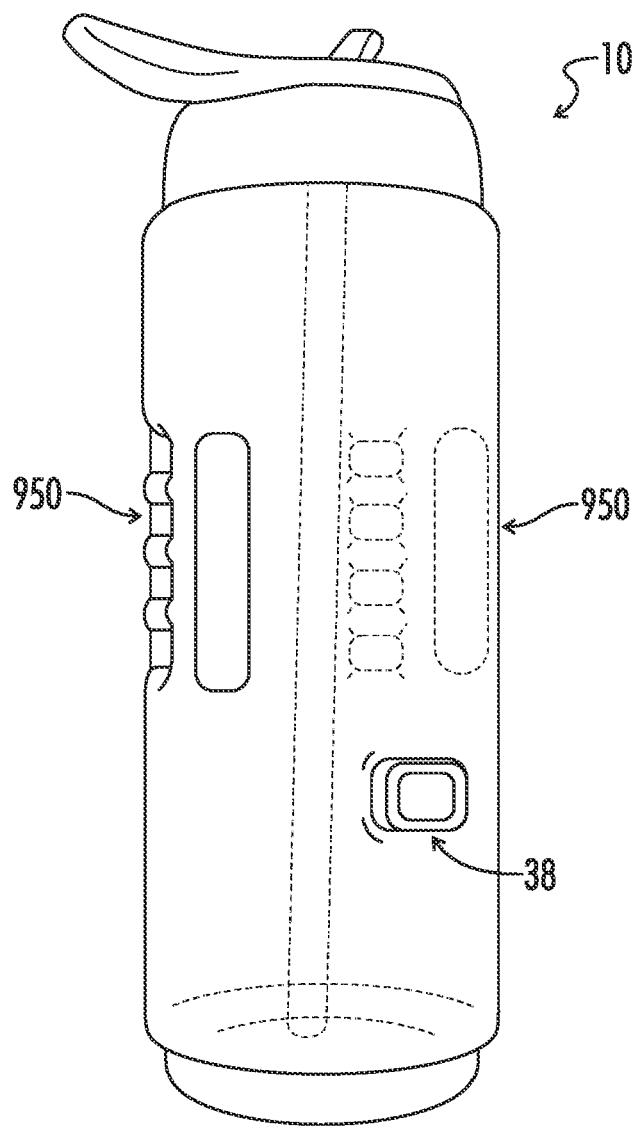
FIG. 33 shows an embodiment of a smart container with finger guides for both hands of a user.

As discussed above, the placement of the electrodes on the smart object has to be able to accommodate different hand size and holding patterns. In one embodiment, a second finger guide may be used to control the placement of the person's second hand. The use of finger guides for both hands can significantly simplify electrode setup. FIG. 33 shows an embodiment of a smart bottle 10 with finger guides 950 and corresponding electrodes (impedance sensors 35) for both hands. The smart bottle 10 can also include an optical sensor 38.

Figure 32:
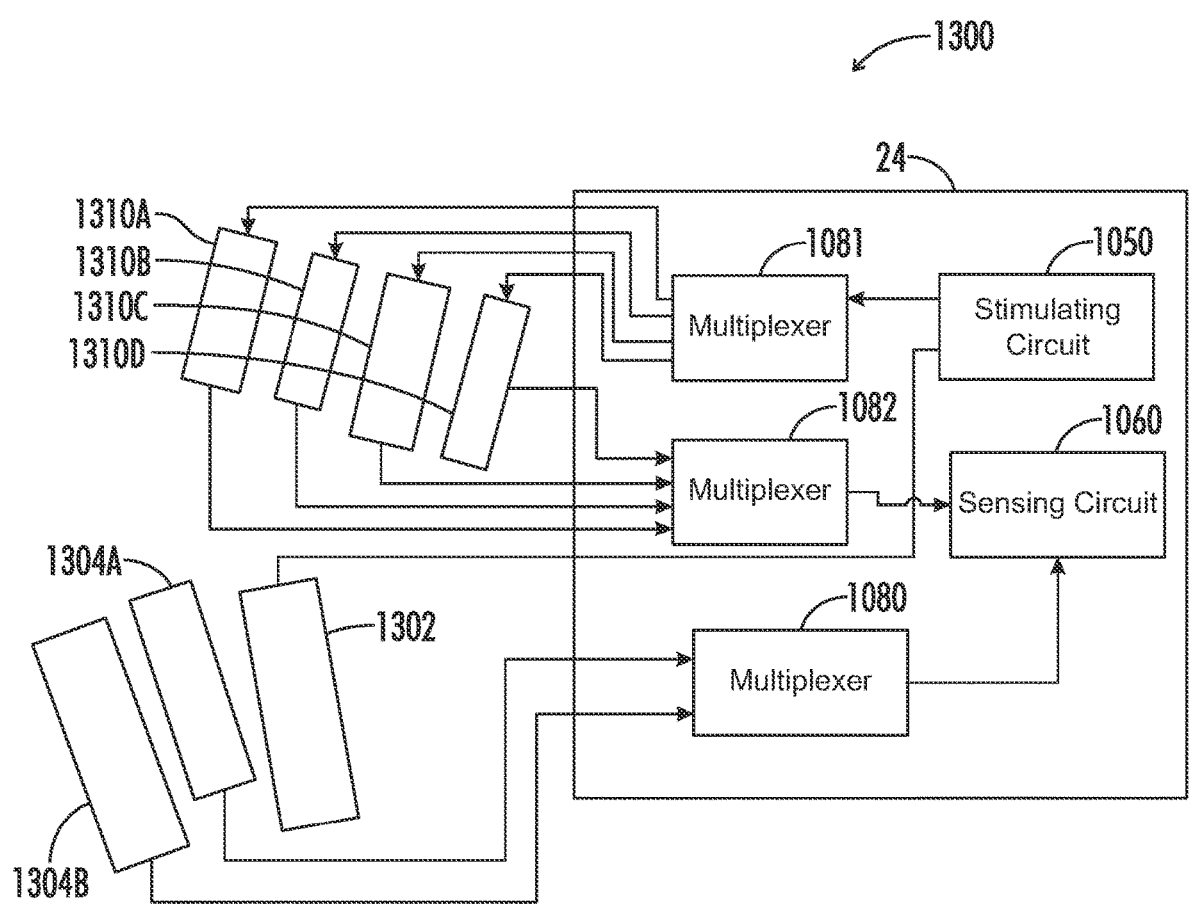

In another embodiment, as shown in FIG. 32, a multitude of electrodes can be used for the second hand of the person in order to make sure the second hand of the person contacts at least two electrodes. The hydration sensing system 1300 shown in FIG. 32 can have stimulation and sensing electrodes for both hands of a person. For one hand of the person, the stimulation electrode 1302 can be placed in proximity to a finger guide located on the smart object 10 and is connected stimulating circuit 1050. Two sensing electrodes 1304A and 1304B can be used on the smart object 10 and connected to sensing circuit 1060 via multiplexer 1080. Similar to the discussion above, the multiplexer 1080 can then select the signal from the electrode 1304A and 1304B that results in the lower absolute value of the impedance—|Z|.

For the other hand of the person, the hydration monitoring system 1300 can use electrodes 1310A-1310D located on the smart object 10 and then select corresponding electrodes from the group of electrodes 1310A-1310D to be the stimulating electrode and the sensing electrode. In an embodiment, the size and shape of each of the electrodes may be varied to best accommodate different hand size and gripping techniques. Each of electrodes 1310A-1310D can be connected to a multiplexer 1081 that is connected to the stimulating circuit 1050 and each of the electrodes 1310A-1310D can be connected to a multiplexer 1082 that is connected to the sensing circuit 1060. The selection of electrodes 1310A-1310D to be the stimulating electrode and the sensing electrode can be determined by the controller 24 (e.g., processor 49) and can correspond to the electrodes that provide for the minimum absolute value of the impedance—|Z|. After automatic selection of electrodes, stimulation would be delivered to "outer" electrodes and response recorded from the "inner" electrodes. For example, stimulation electrodes can be electrodes 1302 and 1310C and sensing electrodes can be electrodes 1304B and 1310A.

Figure 34:
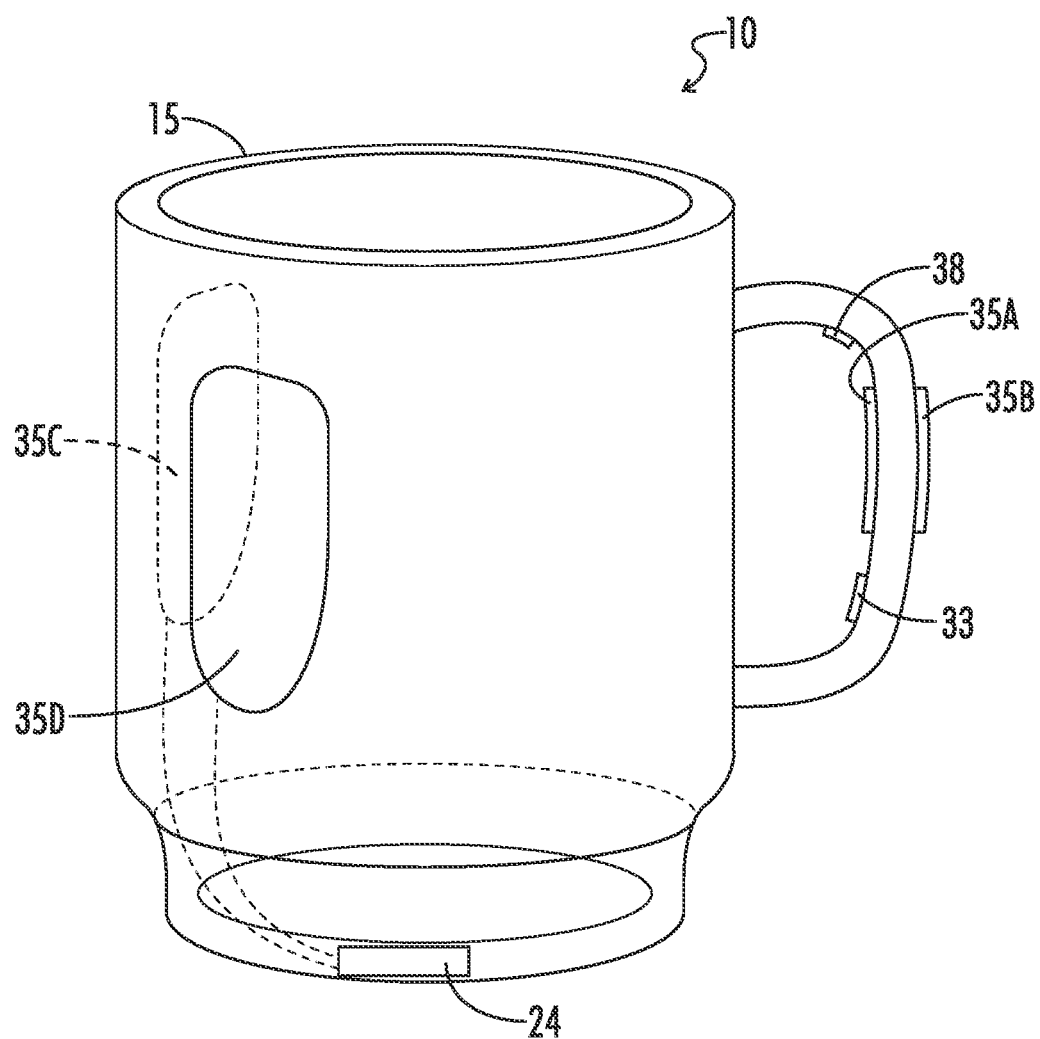
FIG. 34 shows an embodiment of a smart container configured as a mug.

While the smart object 10 has been shown and described with respect to container 11, the smart object 10 and corresponding components (e.g., controller 24 and sensors 14) could be incorporated into a mug, cup or other similar vessel having a handle. FIG. 34 shows an embodiment of a mug or cup configured as a smart object 10. The mug 15 can incorporate a sensing electrode and a stimulation electrode in the handle of the mug 15. In an embodiment, the impedance sensor 35A located on the interior surface of the handle of the mug 15 can be the stimulating electrode and the impedance sensor 35B located on the exterior surface of the handle of the mug 15 can be the sensing electrode, but the stimulating electrode and the sensing electrode may be reversed in other embodiments. In addition, to determine the hydration level of the person across the upper trunk of the person, the mug 15 can include two additional impedance electrodes 35C and 35D (e.g., a sensing electrode and a stimulating electrode) located on the opposite side of the mug 15 from the handle for the other hand of the person (i.e., the hand of the person not holding the handle of the mug 15). Each of the impedance sensors 35A-35D can be connected to the controller 24, which can be located in the base of the mug in an embodiment.

The mug 15 can also include an optic sensor 38 and a motion sensor 33 in the handle or the base of the mug 15. The optic sensor 38 can be used to determine physiological parameters of the person as described above. The motion sensor 33 (e.g., an accelerometer) can be used to determine the position of the mug and to determine the volume of liquid in the mug. In one embodiment, an ECG of the person can be taken between two of the impedance sensors 35A or 35B and 35C or 35D (e.g., impedance sensor 35A on the handle and impedance sensor 35C located on the outside of the mug 15 opposite the handle. In another embodiment, the mug 15 may include a disposable or replaceable internal vessel incorporating impedance sensors 35 that may include spring-loaded contacts for communicating with the controller 24.

Figure 35:
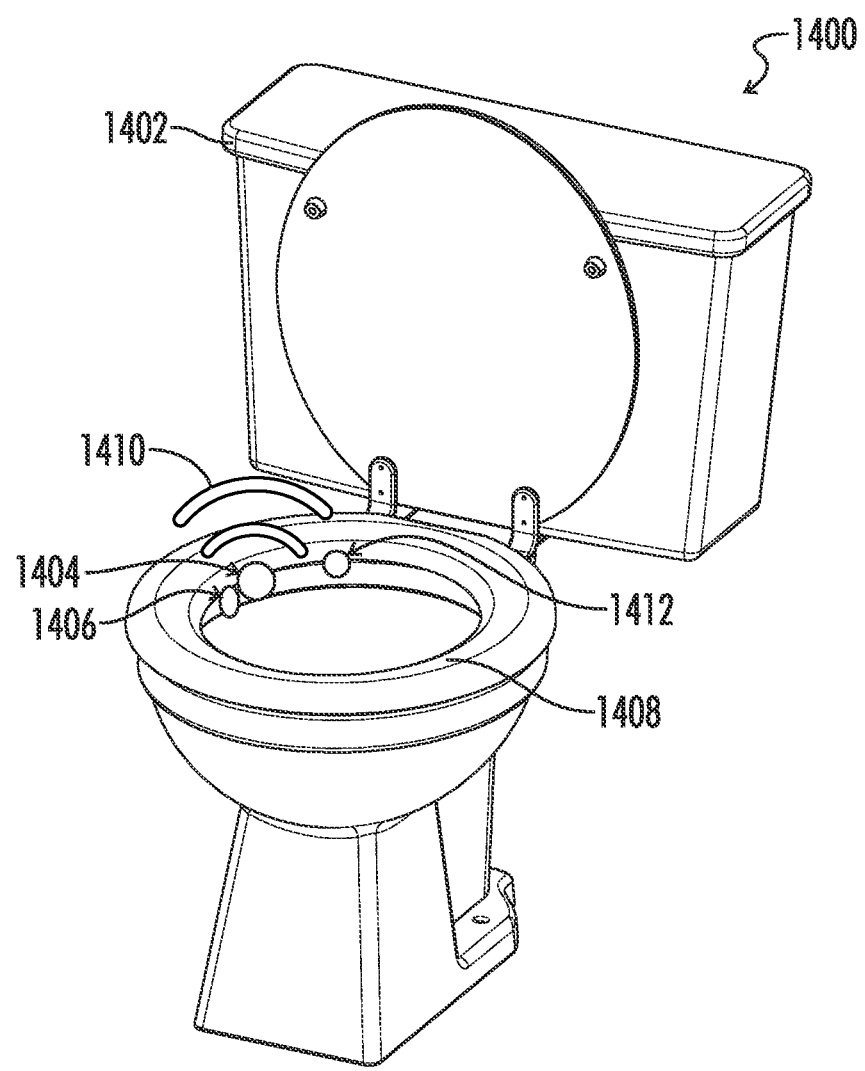
FIG. 35 shows another embodiment of a hydration monitoring system.

In an embodiment, the controller 24 can use changes of heart rate and heart rate variability as determined from the sensors 14 as an indicator of dehydration. In another embodiment, the hydration level of the user may be detected by analyzing the color of the urine of the person, which is a common assessment factor for dehydration. FIG. 35 shows an embodiment of a hydration monitoring system using urine color to determine hydration level. The hydration monitoring system 1400 can be incorporated into a toilet 1402 and detect the color of the urine of the person in the toilet 1402 to determine hydration level of the user. The hydration monitoring system 1400 can implement the automatic analysis of urine color by incorporating into the toilet seat 1408 a controller 1404 (which can be wireless in one embodiment) and a camera 1406 that is connected to the controller 1404 (either by a wired or wireless connection). In addition, the seat 1408 can include a capacitive touch sensor 1410 to detect when a person is using the toilet 1402. When the touch sensor 1410 indicates that a person is using the toilet 1402, the controller 1404 can activate the camera 1408 and a light source 1412 in order to capture an image of the urine within the toilet. The controller 1404 can then analyze the image (e.g., the color of the urine) to determine the hydration level of the user or the controller 1404 can provide the image to the electronic device 70 or the server 60 to perform the analysis of the image.

In an embodiment, the controller 1404 might use scanning of wireless devices (e.g., smart watch 67) to identify the person. The closest user can be identified using strength of the wireless signal, available as a standard parameter called Received Signal Strength Indicator (RSSI). For example, a Bluetooth or BLE (Bluetooth low energy) signal from a smart watch 67 can be used to recognize the user and automatically update the current hydration measurement to the server 60 via network 50.

In other embodiments, the capacitive sensors of touch sensor 38 may be incorporated into other objects or devices in addition to container 11. For example, the capacitive sensors can be incorporated into a watch or bracelet worn by a user or into bands worn around the arms and/or legs of a user. In another example, the capacitive sensors can be incorporated into a necklace or an object hanging from the necklace (e.g., a medical alert device or pendant) that is worn by a user, in a head band or hat worn by a user, or in the frame of glasses worn by a user to provide for continuous monitoring of vital signs of the user. The capacitive sensors can be incorporated into a ring for continuous monitoring of heart activity of a user or incorporated into treadmills, elliptical machines, weights, or other exercise equipment to monitor heart rate during exercise by users. The capacitive sensors can be incorporated into the handle of a cane for continuous monitoring of the elderly or injured users. The capacitive sensors may also be incorporated into everyday objects (e.g., cups and glasses, silverware, kitchen utensils, toothbrushes, hairbrushes, etc.) to detect use and vital signs during the handling of the objects by a user.

In further embodiments, the capacitive sensors of touch sensor 38 can be incorporated into a blood pressure measurement cuff of blood pressure monitor 69 for the monitoring of physiological parameters of the user, such as heart rate, while performing a blood pressure measurement on the user. In another embodiment, the capacitive sensors can continuously and non-invasively monitor the blood pressure of infants in situations where blood pressure measurement cuffs could not be used on the infant. The capacitive sensors can be implemented around a fingerprint sensor to detect vital signs of the user during the fingerprint identification process. In addition, the morphology of the pulse received by the capacitive sensors may assist in the identification of the user.

In an embodiment, physiological parameters (or vital signs) detected on multiple objects can be used to identify who is using a particular object at a particular moment in time. For example, a sequence of RR intervals on a smartwatch 67 can be compared with RR intervals on weights or exercise equipment in a fitness center to determine the person using the equipment. In addition, once the person is identified, the type and intensity of exercise being performed by the person (or user) can be determined. Further, "smart" weights with capacitive sensors can also integrate inertial sensors to determine the number and pace of repetitions being performed by the user during exercise.

In an embodiment, multiple smart objects 10 can be integrated into network 50 and communicate with server 60 (possibly via electronic device 70 as shown in FIG. 3. The smart objects 10 can provide information to the server 60 regarding the use and/or operation of the smart objects 10. For example, the smart object 10 configured as a smart container can provide information on how much liquid has been consumed from the smart object 10, the last time the smart object 10 was used or handled, and/or the corresponding heart rate, respiratory rate, hydration level and/or oxygen saturation in the blood of the user of the smart object 10. A second user (e.g., a healthcare provider) can then access the information for one (or several) smart objects 10 directly from the server 60 and make corresponding evaluations regarding the user of the smart object 10 (e.g., the user needs to hydrate more). In addition, the second user can send alerts or notifications to one or more of the smart objects 10, as needed. In another embodiment, the server 60 can automatically send alerts or notifications to the smart objects 10 when certain data parameters from the smart objects 10 are identified.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

Now, therefore, the following is claimed:

1. A system for monitoring hydration of a user, the system comprising:
   a container configured to hold a liquid;
   at least one sensor comprising a first electrode and a second electrode, the at least one sensor positioned on an exterior surface of the container to permit a tissue of one hand of a user to contact both the first electrode and the second electrode of the at least one sensor when the container is held in the one hand of the user, the at least one sensor configured to sense at least one parameter indicative of a complex impedance of the tissue of the one hand; and
   at least one processor configured to calculate a hydration level for the user based on the at least one parameter indicative of the complex impedance of the tissue of the one hand sensed by the at least one sensor.

2. The system of claim 1, wherein the first electrode is positioned on the object container to contact a first portion of the one hand of the user and the second electrode is positioned on the container to contact a second portion of the one hand of the user different from the first portion when the container is held in the one hand of the user.

3. The system of claim 2, further comprising a stimulation circuit configured to provide stimulation at a preselected frequency between the first electrode and the second electrode and a sensing circuit configured to record a signal between the first electrode and the second electrode.

4. The system of claim 2, wherein the first portion of the one hand corresponds to a finger of the one hand of the user and the second portion corresponds to a palm of the one hand of the user.

5. The system of claim 2, wherein the second electrode comprises a plurality of second electrodes positioned on the exterior surface of the container, wherein at least one second electrode of the plurality of second electrodes contacts the palm of the user when the container is held in the one hand of the user.

6. The system of claim 1, further comprising a guide located on the exterior surface of the container, wherein the first electrode and the second electrode are located on the exterior surface of the container with reference to the guide.

7. The system of claim 1, wherein the at least one sensor comprises a first sensor and a second sensor, the first sensor comprising the first electrode and the second electrode, the second sensor comprising a third electrode and a fourth electrode, the second sensor positioned on an exterior surface of the container to permit a tissue of a second hand of the user to contact both the third electrode and the fourth electrode of the second sensor when the container is held by the second hand of the user, and wherein the first sensor and the second sensor are each configured to sense at least one parameter indicative of a complex impedance of a body of the user.

8. The system of claim 7, wherein the at least one processor is configured to calculate a hydration level for the user based on the at least one parameter indicative of the complex impedance of the body of the user sensed by each of the first sensor and the second sensor.

9. The system of claim 1, wherein the first electrode is positioned on the-container to contact at least one finger of the one hand of the user and the second electrode is positioned on the container to contact a palm of the one hand of the user when the container is held in the one hand of the user.

10. The system of claim 9, further comprising a finger guide located on the exterior surface of the container, wherein the finger guide is a reference point to position the first electrode and the second electrode on the exterior surface of the container.

11. The system of claim 1, further comprising:
    a multiplexer;
    the second electrode comprises a plurality of second electrodes connected to the multiplexer and positioned on the exterior surface of the container, wherein at least one second electrode of the plurality of second electrodes contacts the palm of the user when the container is held in the one hand of the user; and
    the multiplexer is configured to select a signal from a second electrode of the plurality of second electrodes that results in the at least one parameter having a minimum complex impedance of the tissue of the one hand.

12. A system for monitoring hydration of a user, the system comprising:
    an object;
    at least one sensor comprising a first electrode and a second electrode, the at least one sensor positioned on an exterior surface of the object to permit a tissue of one hand of a user to contact both the first electrode and the second electrode of the at least one sensor when the object is held in the one hand of the user, the at least one sensor configured to sense at least one parameter indicative of a complex impedance of the tissue of the one hand;
    a guide located on the exterior surface of the object, wherein the first electrode and the second electrode are located on the exterior surface of the object with reference to the guide, wherein the guide is configured to guide a finger of the user to the first electrode and to guide a palm of the user to the second electrode upon the user interacting with the guide when the object is held in the one hand of the user; and
    at least one processor configured to calculate a hydration level for the user based on the at least one parameter indicative of the complex impedance of the tissue of the one hand sensed by the at least one sensor.

13. A system for monitoring hydration of a user, the system comprising:
    an object;
    at least one sensor comprising a first sensor and a second sensor, the first sensor comprising a first electrode and a second electrode, the second sensor comprising a third electrode and a fourth electrode, the first sensor positioned on an exterior surface of the object to permit a tissue of one hand of a user to contact both the first electrode and the second electrode of the first sensor when the object is held in the one hand of the user, the second sensor positioned on an exterior surface of the object to permit a tissue of a second hand of the user to contact both the third electrode and the fourth electrode of the second sensor when the object is held by the second hand of the user, the first sensor and the second sensor each configured to sense at least one parameter indicative of a complex impedance of a body of the user, wherein the first electrode and the fourth electrode are configured to contact fingers of the user and the second electrode and the third electrode are configured to contact palms of the user; and at least one processor configured to calculate a hydration level for the user based on the at least one parameter indicative of the complex impedance of the body of the user sensed by the first sensor and the second sensor.

14. A method of monitoring hydration of a user, the method comprising:
  positioning a first electrode and a second electrode on an exterior surface of a container configured to hold a liquid to permit a tissue of one hand of a user to contact both the first electrode and the second electrode when the container is held in the one hand of the user;
  sensing, with the first electrode and the second electrode, at least one parameter indicative of a complex impedance of the tissue of the one hand of the user when the container is held in the one hand of the user; and
  calculating, with at least one processor, a hydration level for the user based on the sensed at least one parameter indicative of the complex impedance of the tissue of the one hand.

15. The method of claim 14, wherein sensing the at least one parameter includes:
  providing, with a stimulation circuit, stimulation at a preselected frequency between the first electrode and the second electrode; and
  recording, with a sensing circuit, a signal between the first electrode and the second electrode.

16. The method of claim 14, further comprising:
  positioning a third electrode and a fourth electrode on the exterior surface of the container to permit a tissue of a second hand of the user to contact both the third electrode and the fourth electrode when the container is held by the second hand of the user; and
  sensing at least one parameter indicative of a complex impedance of a body of the user when the container is held by both hands of the user, wherein the sensing at least one parameter indicative of the complex impedance of the body of the user includes:
    providing, with a stimulation circuit, stimulation at a preselected frequency to the first electrode and the fourth electrode; and
    recording, with a sensing circuit, a signal at the second electrode and the third electrode.

17. The method of claim 16, further comprising calculating, with the at least one processor, a hydration level for the user based on the sensed at least one parameter indicative of the complex impedance of the body of the user.

18. The method of claim 16, wherein the first electrode and the fourth electrode are configured to contact fingers of the one hand and second hand of the user and the second electrode and the third electrode are configured to contact palms of the one hand and second hand of the user.

19. The method of claim 14, further comprising:
  positioning a guide on the exterior surface of the container;
  wherein positioning the first electrode and the second electrode on the exterior surface of the container further includes locating the first electrode and the second electrode on the exterior surface of the container with reference to the guide; and
  the guide is configured to guide a finger of the user to the first electrode and to guide a palm of the user to the second electrode upon the user interacting with the guide when the container is held in the one hand of the user.

20. The method of claim 14, wherein positioning the first electrode and the second electrode on the exterior surface of the container further includes positioning the first electrode on the container to contact a finger of the one hand of the user and positioning the second electrode on the container to contact a palm of the one hand of the user when the container is held in the one hand of the user.

* * * * *